United States Patent
Blair

(10) Patent No.: US 10,285,775 B2
(45) Date of Patent: May 14, 2019

(54) APPARATUSES TO PHYSICALLY COUPLE TRANSPONDER TO OBJECTS, SUCH AS SURGICAL OBJECTS, AND METHODS OF USING SAME

(71) Applicant: Covidien LP, Mansfield, MA (US)

(72) Inventor: William A. Blair, San Diego, CA (US)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 15/053,956

(22) Filed: Feb. 25, 2016

(65) Prior Publication Data

US 2016/0250000 A1    Sep. 1, 2016

Related U.S. Application Data

(60) Provisional application No. 62/121,358, filed on Feb. 26, 2015.

(51) Int. Cl.
| | |
|---|---|
| *A61B 90/00* | (2016.01) |
| *A61B 90/98* | (2016.01) |
| *G06K 7/10* | (2006.01) |

(52) U.S. Cl.
CPC .......... *A61B 90/98* (2016.02); *G06K 7/10128* (2013.01)

(58) Field of Classification Search
CPC ............................ A61B 90/98; G06K 7/10128
See application file for complete search history.

(56) References Cited

U.S. PATENT DOCUMENTS

| | | | |
|---|---|---|---|
| 2,740,405 | A | 4/1956 | Riordan |
| 3,031,864 | A | 5/1962 | Freundlich |
| 3,587,583 | A | 6/1971 | Greenberg |
| 3,630,202 | A | 12/1971 | Small |
| 4,114,601 | A | 9/1978 | Abels |
| 4,193,405 | A | 3/1980 | Abels |

(Continued)

FOREIGN PATENT DOCUMENTS

| | | |
|---|---|---|
| AU | 2003249257 A1 | 2/2004 |
| CN | 101460096 A | 6/2009 |

(Continued)

OTHER PUBLICATIONS

Bacheldor, "Surgical Sponges Get Smart" *RFID Journal*, Jul. 26, 2006, 2 pages.

(Continued)

*Primary Examiner* — Richard Chang

(57) ABSTRACT

Apparatuses and methods to physically couple a transponder to a surgical object are provided. One example apparatus includes a first clamp comprising a first fastener and a first channel member that has a first base and a first pair of side portions that extend from the first base to form a first channel therebetween. The first fastener adjustably engages with the first channel member to securingly clamp a surgical object in the first channel of the first channel member. The apparatus further includes a housing that has at least a first cavity that receives at least a portion of the first pair of side portions of the first channel member, a first passageway that receives the first fastener and permits the first fastener to extend at least in part into the first cavity, and a second passageway to receive at least one transponder that wirelessly receives and returns signals.

20 Claims, 23 Drawing Sheets

(56) References Cited

U.S. PATENT DOCUMENTS

| | | |
|---|---|---|
| D272,943 S | 5/1984 | Stone et al. |
| 4,477,256 A | 10/1984 | Hirsch |
| 4,626,251 A | 12/1986 | Shen |
| 4,893,118 A | 1/1990 | Lewiner et al. |
| 4,935,019 A | 6/1990 | Papp, Jr. |
| 5,057,095 A | 10/1991 | Fabian |
| 5,090,410 A | 2/1992 | Saper et al. |
| 5,105,829 A | 4/1992 | Fabian et al. |
| 5,112,325 A | 5/1992 | Zachry |
| D330,872 S | 11/1992 | Ball |
| 5,181,021 A | 1/1993 | Lee et al. |
| 5,224,593 A | 7/1993 | Bennett |
| 5,235,326 A | 8/1993 | Beigel et al. |
| 5,329,944 A | 7/1994 | Fabian et al. |
| D353,343 S | 12/1994 | Eberhardt |
| D354,927 S | 1/1995 | Andrau |
| D356,052 S | 3/1995 | Andrau |
| D359,705 S | 6/1995 | Ball |
| 5,650,596 A | 7/1997 | Morris et al. |
| 5,664,582 A | 9/1997 | Szymaitis |
| D412,135 S | 7/1999 | Saito |
| 5,923,001 A | 7/1999 | Morris et al. |
| 5,963,132 A * | 10/1999 | Yoakum ............ A01K 11/006 128/899 |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassøe |
| 6,093,869 A | 7/2000 | Roe et al. |
| 6,276,033 B1 | 8/2001 | Johnson et al. |
| 6,366,206 B1 | 4/2002 | Ishikawa et al. |
| D456,907 S | 5/2002 | Sanfilippo |
| 6,384,296 B1 | 5/2002 | Roe et al. |
| 6,441,741 B1 | 8/2002 | Yoakum |
| D471,281 S | 3/2003 | Baura et al. |
| 6,632,216 B2 | 10/2003 | Houzego et al. |
| 6,654,629 B2 | 11/2003 | Montegrande |
| 6,734,795 B2 | 5/2004 | Price |
| 6,753,783 B2 | 6/2004 | Friedman et al. |
| D495,055 S | 8/2004 | Silber |
| 6,777,623 B2 | 8/2004 | Ballard |
| 6,778,089 B2 | 8/2004 | Yoakum |
| 6,812,842 B2 | 11/2004 | Dimmer |
| 6,822,570 B2 | 11/2004 | Dimmer et al. |
| 6,838,990 B2 | 1/2005 | Dimmer |
| D502,419 S | 3/2005 | Copen |
| 6,861,954 B2 | 3/2005 | Levin |
| 6,875,199 B2 | 4/2005 | Altman |
| 6,879,300 B2 | 4/2005 | Rochelle et al. |
| 6,998,541 B2 | 2/2006 | Morris et al. |
| 7,001,366 B2 | 2/2006 | Ballard |
| 7,019,650 B2 | 3/2006 | Volpi et al. |
| 7,026,927 B2 | 4/2006 | Wright et al. |
| 7,037,336 B2 | 5/2006 | Ward |
| D526,586 S | 8/2006 | McCaghren et al. |
| 7,098,793 B2 | 8/2006 | Chung |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| D534,448 S | 1/2007 | Shaffer, II et al. |
| 7,158,030 B2 | 1/2007 | Chung |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,399,899 B2 | 7/2008 | Fabian |
| 7,420,468 B2 | 9/2008 | Fabian et al. |
| 7,423,535 B2 | 9/2008 | Chung et al. |
| 7,449,614 B2 | 11/2008 | Ales, III |
| 7,464,713 B2 | 12/2008 | Fabian et al. |
| 7,465,847 B2 | 12/2008 | Fabian |
| 7,474,222 B2 | 1/2009 | Yang et al. |
| 7,492,261 B2 | 2/2009 | Cambre et al. |
| 7,492,263 B2 | 2/2009 | Marsilio et al. |
| 7,508,308 B2 | 3/2009 | Chung |
| 7,513,425 B2 | 4/2009 | Chung |
| 7,557,710 B2 | 7/2009 | Sanchez et al. |
| D598,114 S | 8/2009 | Cryan |
| 7,596,850 B2 | 10/2009 | Barth et al. |
| 7,644,016 B2 | 1/2010 | Nycz et al. |
| 7,696,877 B2 | 4/2010 | Barnes et al. |
| 7,795,491 B2 | 9/2010 | Stewart et al. |
| 7,837,694 B2 | 11/2010 | Tethrake et al. |
| 7,898,420 B2 | 3/2011 | Blair et al. |
| 8,181,860 B2 | 5/2012 | Fleck et al. |
| 8,193,938 B2 | 6/2012 | Halberthal et al. |
| 8,358,212 B2 | 1/2013 | Blair |
| 8,454,613 B2 | 6/2013 | Tethrake et al. |
| 8,477,076 B1 | 7/2013 | Nero, Jr. et al. |
| 8,624,721 B2 | 1/2014 | Barker, Jr. et al. |
| 8,710,957 B2 | 4/2014 | Blair et al. |
| 8,726,911 B2 | 5/2014 | Blair |
| 8,872,662 B2 | 10/2014 | Halberthal et al. |
| 8,994,358 B2 | 3/2015 | McElhinny et al. |
| 9,041,479 B2 | 5/2015 | Nero, Jr. et al. |
| 9,089,366 B2 | 7/2015 | Garner-Richards et al. |
| 9,144,466 B2 | 9/2015 | McElhinny et al. |
| 9,414,973 B2 | 8/2016 | Fleck et al. |
| 9,672,397 B2 | 6/2017 | Fleck et al. |
| 2001/0000659 A1 | 5/2001 | Hayashi et al. |
| 2001/0030610 A1 | 10/2001 | Rochelle et al. |
| 2002/0032435 A1 | 3/2002 | Levin |
| 2002/0070863 A1 | 6/2002 | Brooking |
| 2002/0188259 A1 | 12/2002 | Hickle et al. |
| 2003/0004411 A1 | 1/2003 | Govari et al. |
| 2003/0105394 A1 | 6/2003 | Fabian et al. |
| 2004/0008123 A1 | 1/2004 | Carrender et al. |
| 2004/0129279 A1 | 7/2004 | Fabian et al. |
| 2004/0138554 A1 | 7/2004 | Dimmer et al. |
| 2004/0250819 A1 | 12/2004 | Blair et al. |
| 2004/0254420 A1 | 12/2004 | Ward |
| 2005/0049564 A1 | 3/2005 | Fabian |
| 2005/0154293 A1 | 7/2005 | Gisselberg et al. |
| 2005/0203470 A1 | 9/2005 | Ballard |
| 2006/0054107 A1 | 3/2006 | Baker |
| 2006/0084934 A1 | 4/2006 | Frank |
| 2006/0106368 A1 | 5/2006 | Miller et al. |
| 2006/0187044 A1 | 8/2006 | Fabian et al. |
| 2006/0194899 A1 | 8/2006 | Ohashi et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2007/0004994 A1 | 1/2007 | Sherman |
| 2007/0005141 A1 | 1/2007 | Sherman |
| 2007/0034670 A1 | 2/2007 | Racenet et al. |
| 2007/0038233 A1 | 2/2007 | Martinez et al. |
| 2007/0051473 A1 | 3/2007 | Speich |
| 2007/0055109 A1 | 3/2007 | Bass et al. |
| 2007/0112649 A1 | 5/2007 | Schlabach |
| 2007/0125392 A1 | 6/2007 | Olson, Jr. et al. |
| 2007/0216062 A1 | 9/2007 | Frank |
| 2007/0216526 A1 | 9/2007 | Volpi et al. |
| 2007/0239289 A1 | 10/2007 | Cambre et al. |
| 2007/0265690 A1 | 11/2007 | Lichtenstein et al. |
| 2008/0007411 A1 | 1/2008 | Levin |

(56) References Cited

U.S. PATENT DOCUMENTS

| | | | |
|---|---|---|---|
| 2008/0018432 A1 | 1/2008 | Volpi et al. | |
| 2008/0020189 A1 | 1/2008 | Hofmair et al. | |
| 2008/0021308 A1 | 1/2008 | Dimmer et al. | |
| 2008/0024277 A1 | 1/2008 | Volpi et al. | |
| 2008/0231452 A1 | 9/2008 | Levin | |
| 2008/0238677 A1* | 10/2008 | Blair | A61B 5/06 340/572.1 |
| 2008/0281190 A1 | 11/2008 | Petcavich et al. | |
| 2008/0296373 A1 | 12/2008 | Zmood et al. | |
| 2009/0267765 A1 | 10/2009 | Greene et al. | |
| 2009/0322485 A1 | 12/2009 | Barnes et al. | |
| 2010/0033309 A1 | 2/2010 | Blair | |
| 2010/0179822 A1 | 7/2010 | Reppas | |
| 2011/0181394 A1 | 7/2011 | Blair | |
| 2011/0277359 A1 | 11/2011 | Halberthal et al. | |
| 2012/0031547 A1 | 2/2012 | Halberthal et al. | |
| 2013/0088354 A1 | 4/2013 | Thomas | |
| 2013/0199720 A1 | 8/2013 | Halberthal et al. | |
| 2014/0068915 A1 | 3/2014 | Halberthal et al. | |
| 2015/0164603 A1 | 6/2015 | Fleck et al. | |
| 2015/0216610 A1 | 8/2015 | Augustine | |
| 2015/0317555 A1 | 11/2015 | Dor et al. | |
| 2016/0157957 A1 | 6/2016 | Blair | |
| 2016/0206399 A1 | 7/2016 | Blair | |
| 2016/0210548 A1 | 7/2016 | Blair | |
| 2016/0250000 A1 | 9/2016 | Blair | |
| 2016/0259954 A1 | 9/2016 | Buhler et al. | |
| 2018/0000555 A1 | 1/2018 | Blair | |
| 2018/0000556 A1 | 1/2018 | Blair | |

FOREIGN PATENT DOCUMENTS

| | | |
|---|---|---|
| EP | 2 087 850 A2 | 8/2009 |
| JP | 2009539478 A | 11/2009 |
| WO | 86/02539 A1 | 5/1986 |
| WO | 02/39917 A1 | 5/2002 |
| WO | 2004/008387 A1 | 1/2004 |
| WO | 2004/086997 A1 | 10/2004 |
| WO | 2006/060781 A1 | 6/2006 |
| WO | 2007/146091 A1 | 12/2007 |
| WO | 2008/024921 A1 | 2/2008 |
| WO | 2008/106552 A1 | 9/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |

OTHER PUBLICATIONS

Blair et al., "Method and Apparatus to Detect Transponder Tagged Objects and to Communicate with Medical Telemetry Devices, for Example During Medical Procedures," U.S. Appl. No. 61/242,699, filed Sep. 15, 2009, 158 pages.

Blair et al., "Method and Apparatus to Detect Transponder Tagged Objects and to Communicate with Medical Telemetry Devices, for Example During Surgery," U.S. Appl. No. 61/222,847, filed Jul. 2, 2009, 122 pages.

Blair, "Transponder Device to Mark Implements, Such as Surgical Implements, and Method of Manufacturing and Using Same," U.S. Appl. No. 61/224,323, filed Jul. 9, 2009, 57 pages.

Blair, "Wirelessly Detectable Objects for Use in Medical Procedures and Methods of Making Same," U.S. Appl. No. 62/138,248, filed Mar. 25, 2015, 67 pages.

International Search Report and Written Opinion, dated May 2, 2016, for International Application No. PCT/US2016/014324, 18 pages.

International Search Report, dated May 13, 2016, for International Application No. PCT/US2016/014335, 3 pages.

Merritt et al., "Detectable Sponges for Use in Medical Procedures and Methods of Making, Packaging, and Accounting for Same," U.S. Appl. No. 15/540,331, filed Jun. 28, 2017, 54 pages.

Technologies Solutions Group, "Sponge-Track," 2013, 2 pages.

Blair et al., "Tag and Detection Device," U.S. Appl. No. 60/458,222, filed Mar. 27, 2003, 23 pages.

Blair et al., "Improved Apparatus and Method for Detecting Objects Using Tags and Wideband Detection Device," U.S. Appl. No. 60/811,376, filed Jun. 6, 2006, 16 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Transponder Housing and Device to Mark Implements, Such as Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Barnes et al., "Method, Apparatus and Article for Detection of Transponder Tagged Objects, for Example During Surgery," U.S. Appl. No. 61/056,787, filed May 28, 2008, 60 pages.

Blair, "Transponder Device to Mark Implements, Such as Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair, "Multi-Modal Transponder and Method and Apparatus to Detect Same," U.S. Appl. No. 61/102,749, filed Oct. 3, 2008, 48 pages.

Blair, "Detectable Surgical Objects and Methods of Making Same," U.S. Appl. No. 61/109,142, filed Oct. 28, 2008, 47 pages.

Blair, "Radio Opaque Device With Resonant Nanostructures," U.S. Appl. No. 61/163,813, filed Mar. 26, 2009, 47 pages.

Blair, "Transponder Device to Mark Implements, Such as Surgical Implements, and Method of Manufacturing and Using Same," U.S. Appl. No. 61/220,452, filed Jun. 25, 2009, 46 pages.

Blair et al., "Method and Apparatus to Detect Transponder Tagged Objects, for Example During Medical Procedures," U.S. Appl. No. 61/242,704, filed Sep. 15, 2009, 127 pages.

Blair, "Method and Apparatus to Account for Transponder Tagged Objects Used During Medical Procedures," U.S. Appl. No. 61/263,726, filed Nov. 23, 2009, 78 pages.

Blair, "Wirelessly Detectable Objects for Use in Medical Procedures and Methods of Making Same," U.S. Appl. No. 62/106,052, filed Jan. 21, 2015, 49 pages.

Blair, "Transponder Housing," Design U.S. Appl. No. 29/322,539, filed Aug. 6, 2008, 6 pages.

Blair, "Attachment Article to Attach a Transponder to a Surgical Sponge," Design U.S. Appl. No. 29/336,007, filed Apr. 27, 2009, 4 pages.

Blair, "Attachment Article to Attach a Transponder to a Surgical Sponge," Design U.S. Appl. No. 29/336,008, filed Apr. 27, 2009, 7 pages.

Blair, "Article to Attach a Transponder to a Surgical Sponge," Design U.S. Appl. No. 29/336,009, filed Apr. 27, 2009, 4 pages.

Blair, "Apparatuses to Physically Couple Transponder to Objects, Such as Surgical Objects, and Methods of Using Same," U.S. Appl. No. 62/121,358, filed Feb. 26, 2015, 88 pages.

Clearcount Medical Solutions, "The SmartSponge System," Downloaded from http://clearcount.com on Oct. 20, 2009, 7 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

* cited by examiner

APPARATUSES TO PHYSICALLY COUPLE TRANSPONDER TO OBJECTS, SUCH AS SURGICAL OBJECTS, AND METHODS OF USING SAME

BACKGROUND

Technical Field

The present disclosure generally relates to surgical objects. More particularly, the present disclosure relates to apparatuses and methods to physically couple a transponder to a surgical object.

Description of the Related Art

It is often useful or important to be able to determine the presence or absence of a foreign object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures, which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system may include a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

BRIEF SUMMARY

Commercial implementation of such a wireless interrogation and detection system requires that the overall system be cost effective and highly accurate. In particular, false negatives must be avoided to ensure that objects are not mistakenly left in the patient. The overall automated system requires a large number of transponders, since at least one transponder is carried, attached or otherwise coupled to each object which may or will be used in surgery. Consequently, the transponders and apparatuses for carrying, attaching or coupling the transponder to the object should be inexpensive.

It may be possible for the apparatuses that carry, attach, or couple the transponder to the object to hinder accurate detection of the transponder. For instance, if the object and/or the apparatus carrying the transponder is metallic or other metallic objects are present in the body, a transponder that is in fact present may not be able to be detected as a result of the metallic object acting as a Faraday shield or otherwise interfering with transponder communications. As such, an apparatus to physically couple the transponder to the object should not impede accurate detection of the transponder.

Furthermore, certain surgical objects may undergo one or more rounds of sterilization before and/or after use within the surgical environment. If the transponder is employed to track use and sterilization of the surgical object, for example, the apparatus that physically couples the transponder to the object may remain attached to the surgical object during such sterilization procedures. If the apparatus is unable to withstand such sterilization processes, the apparatus may insufficiently protect the transponder from certain hazards of the sterilization process. Therefore, an apparatus that is capable of withstanding different sterilization processes is desirable.

In other instances, it may be desirable to remove the apparatus containing the transponder from a surgical object. For example, the apparatus can be removed, separately sterilized, and then reused with a different surgical object used in a subsequent surgical event. Such may advantageously allow use of a single set of apparatuses/transponders in multiple different surgical environments that respectively require different sets of surgical objects. Therefore, an apparatus that is capable of being removed from the surgical object is desirable.

Consequently, an inexpensive, durable, reusable, and/or non-interfering apparatus to physically couple a transponder to a surgical object is highly desirable.

An apparatus to physically couple one or more transponders to a surgical object used in a surgical environment may be summarized as including: at least a first clamp comprising a first fastener and a first channel member, the first channel member having a first base and a first pair of side portions that extend from the first base and which are opposed to one another across a width of the first channel member to form a first channel therebetween, the width of the first channel sized to receive at least a first portion of a surgical object therein, wherein the first fastener adjustably engages with the first channel member to securingly clamp the first portion of the surgical object in the first channel of the first channel member; a housing that has at least a first cavity that receives at least a portion of the first pair of side portions of the first channel member, a first passageway that receives the first fastener and opens at least in part into the first cavity to permit the first fastener to extend at least in part into the first cavity and adjustably engage with the first channel member, and a second passageway to receive at least one transponder that wirelessly receives and returns signals.

The apparatus may further include: a second clamp comprising a second fastener and a second channel member, the second channel member having a second base and a second pair of side portions that extend from the second base and which are opposed to one another across a width of the second channel member to form a second channel therebetween, the width of the second channel sized to receive at least a second portion of the surgical object therein, wherein the second fastener adjustably engages with the second channel member to securingly clamp the second portion of the surgical object in the second channel of the second channel member. The housing may include a second cavity that receives at least a portion of the second pair of side portions of the second channel member and a third passageway that receives the second fastener and opens at least in part into the second cavity to permit the second fastener to extend at least in part into the second cavity and adjustably engage with the second channel member. The apparatus may further include: the at least one transponder received in the second passageway. The first passageway may extend in a first direction, the second passageway may extend in a second direction, and the third passageway may extend in a third direction, the third direction parallel to the first direction, the second direction non-parallel with respect to the first and the third directions. The first fastener and the second fastener may respectively include an elongated shaft that has a first diameter and a head that has a second diameter that is greater than the first diameter, and the first passageway and the third passageway may respectively include an outer portion that has a third diameter that is greater than the second diameter and an inner portion that has a fourth diameter that is greater than the first diameter and less than the second diameter. The second passageway may intersect the outer portion of the first passageway, the second passageway having a fifth diameter at least greater than the second diameter. The second passageway may intersect the inner portion of the first passageway, and the second passageway may include a fifth diameter at least greater than the first diameter. The housing may form a first shelf at a first transition between the outer portion and the inner portion of the first passageway, the first shelf may physically engage the head of the first fastener, the housing may form a second shelf at a second transition between the outer portion and the inner portion of the third passageway, and the second shelf may physically engage the head of the second fastener. The first fastener may include a first externally threaded screw and a first internally threaded nut that securingly receives the first externally threaded screw, the first channel member may further include a first pair of flanges that respectively extend from the first pair of side portions into the first channel, and the first internally threaded nut may be positioned between the first pair of flanges and the first base and physically engages the first pair of flanges. The first fastener may include a first externally threaded screw and a first internally threaded nut that securingly receives the first externally threaded screw, the first channel member may further include a first pair of flanges that respectively extend from the first pair of side portions into the first channel, and the first internally threaded nut may be positioned opposite the first pair of flanges from the first base. The first fastener may include a first screw that has first external threading, and the first channel member may further include a first pair of flanges that respectively extend from the first pair of side portions into the first channel and engage the first external threading of the first screw. The first pair of flanges may respectively include respective end portions that are respectively angled towards the first base of the first channel member and engage the first external threading of the first screw. A length of each of the first pair of side portions taperedly may increase as the respective side portion extends away from the first base. The first channel member may further include a first pair of flanges that respectively extend from the first pair of side portions into the first channel and respectively have a through-hole extending therethrough, the respective through-holes of the first pair of flanges are aligned, and the first fastener extends through the through-holes of the first pair of flanges. The apparatus may further include: an encapsulant that fills at least one of the first passageway or the second passageway. The encapsulant may be capable of withstanding sterilization of the apparatus by one or more of autoclaving, electron beam or isotope radiation, ethylene oxide, plasma or corona discharge, and liquid sterilants. The encapsulant may include a biocompatible epoxy.

A method to physically couple one or more transponders to a surgical object usable in a surgical environment may be summarized as including: positioning a first portion of a surgical object into a first channel formed by a first channel member, the first channel member having a first base and a first pair of side portions that extend from the first base and which are opposed to one another across a width of the first channel member to form the first channel therebetween; positioning a housing that has a first cavity, a first passageway that opens at least in part into the first cavity, and a second passageway therein to receive at least a portion of the first pair of side portions in the first cavity, the second passageway sized to receive at least one transponder; inserting a first fastener into the first passageway to engage the first channel member; and adjusting a first engagement between the first fastener and the first channel member to securingly clamp the first portion of the surgical object in the first channel of the first channel member.

The method may further include: adjusting the first engagement to release the first portion of the surgical object from the first channel of the first channel member; and removing the housing from the surgical object. The method may further include: positioning a second portion of the surgical object into a second channel formed by a second first channel member, the second channel member having a second base and a second pair of side portions that extend from the second base and which are opposed to one another across a width of the second channel member to form the second channel therebetween; positioning the housing to receive at least a portion of the second pair of side portions in a second cavity of the housing; inserting a second fastener into a third passageway of the housing to engage the second channel member; and adjusting a second engagement between the second fastener and the second channel member to securingly clamp the second portion of the surgical object in the second channel of the second channel member. The method may further include: inserting the at least one transponder into the second passageway. Inserting the at least one transponder into the second passageway may include inserting the at least one transponder into the second passageway that intersects with the first passageway to move the at least one transponder past the first passageway. The method may further include: filling each of the first and the second passageways with an encapsulant. Inserting a first fastener may include inserting a first screw that has first external threading into the first passageway, and adjusting a first engagement may include rotating the first screw to engage the first external threading of the first screw with one or more of i) a first and a second lip of the first channel member that respectively extend from the first pair of side portions into the first channel and ii) a first nut located above or below the first and the second lip and engaged therewith.

An apparatus to physically couple one or more transponders to a surgical object used in a surgical environment may be summarized as including a housing that has a first cavity that has a first body portion and a first pair of leg portions that respectively extend from the first body portion in a first direction; a first channel member having a first base and a first pair of side portions that extend from the first base and which are opposed to one another across a width of the first channel member to form a first channel therebetween, the width of the first channel sized to receive at least a first portion of the surgical object therein, the first pair of side portions which respectively extend through the first pair of leg portions to reach the first body portion, the first pair of side portions of the first channel member physically secured to each other within the first body portion of the first cavity to physically secure the first channel member with respect to the housing and clamp the first portion of the surgical object in the first channel. The first pair of side portions of the first channel member may be twisted together in the first body portion of the first cavity to physically secure the first channel member with respect to the housing. The first pair of side portions may respectively have a first pair of end portions opposite the first base, the first pair of end portions which extend into the first channel and respectively have a first pair of complementary helical structures that physically engage each other.

The apparatus may further include at least one transponder received in the housing and physically surrounded and engaged by one of the housing or an encapsulant, the at least one transponder to wirelessly receive and return signals.

A method to physically couple one or more transponders to a surgical object usable in a surgical environment may be summarized as including positioning a first portion of a surgical object into a first channel formed by a first channel member, the first channel member having a first base and a first pair of side portions that extend from the first base and which are opposed to one another across a width of the first channel member to form the first channel therebetween; positioning a housing that has a first cavity that has a first body portion and a first pair of leg portions that respectively extend from the first body portion in a first direction to respectively receive the first pair of side portions in the first pair of leg portions of the first cavity and permit the first pair of side portions to extend into the first body portion of the first cavity; and physically securing the first pair of side portions to each other in the first body portion of the first cavity to physically secure first channel member with respect to the housing and securingly clamp the first portion of the surgical object in the first channel of the first channel member. Physically securing the first pair of side portions to each other may include twisting the first pair of side portions together in the first body portion of the first cavity. Physically securing the first pair of side portions to each other may include physically engaging a first pair of complementary helical structures with each other, the first pair of complementary helical structures at respective first end portions of the first pair of side portions opposite the first base.

The method may further include physically unsecuring the first channel member with respect to the housing to unclamp the first portion of the surgical object from the first channel of the first channel member.

The method may further include molding or potting at least one transponder into the housing.

An apparatus to physically couple one or more transponders to a surgical object used in a surgical environment may be summarized as including a first channel member having a first base, a first pair of side portions, and a first pair of flanges, the first pair of side portions which extend from the first base and which are opposed to one another across a width of the first channel member to form a first channel therebetween, the width of the first channel sized to receive at least a first portion of the surgical object therein, the first pair of flanges which respectively extend from the first pair of side portions into the first channel; and a housing that has a first pair of cavities to respectively receive at least the first pair of flanges and a plurality of pairs of teeth respectively defined in the first pair of cavities to permit the first channel member to be physically secured with respect to the housing at a plurality of different positions that respectively correspond to a plurality of different channel heights for the first channel, the first pair of flanges respectively engaged with at least a respective one of the plurality of pairs of teeth.

The apparatus may further include at least one transponder received in the housing and physically surrounded and engaged by one of the housing or an encapsulant, the at least one transponder to wirelessly receive and return signals.

A method to physically couple one or more transponders to a surgical object usable in a surgical environment may be summarized as including positioning a first portion of a surgical object into a first channel formed by a first channel member, the first channel member having a first base, a first pair of side portions, and a first pair of flanges, the first pair of side portions which extend from the first base and which are opposed to one another across a width of the first channel member to form a first channel therebetween, the width of the first channel sized to receive at least a first portion of the surgical object therein, the first pair of flanges which respectively extend from the first pair of side portions into the first channel; positioning a housing that has a first pair of cavities to respectively receive at least the first pair of flanges in the first pair of cavities, a plurality of pairs of teeth respectively spaced at different positions in the first pair of cavities, the plurality of pairs of teeth which respectively extend into the first pair of cavities; and causing the first pair of flanges of the first channel member to respectively engage with a respective pair of the plurality of pairs of teeth to physically secure first channel member with respect to the housing and securingly clamp the first portion of the surgical object in the first channel of the first channel member.

The method may further include physically unsecuring the first channel member with respect to the housing to unclamp the first portion of the surgical object from the first channel of the first channel member.

The method may further include molding or potting at least one transponder into the housing.

An apparatus to physically couple one or more transponders to a surgical object used in a surgical environment may be summarized as including a housing comprising a male body portion and a female body portion, the male body portion comprising at least one member that extends from the male body portion, the female body portion comprising at least one slot sized and shaped to fittingly receive the at least one member of the male body portion, the housing adjustable between a closed configuration in which the at least one member of the male body portion is physically engaged with the at least slot of the female body portion and an open configuration in which the at least one member of the male body portion is not physically engaged with the at least slot of the female body portion; and a first channel member that has a first base and a first pair of side portions that extend from the first base and which are opposed to one another across a width of the first channel member to form a first channel therebetween, the width of the first channel sized to receive at least a first portion of a surgical object therein, the first channel member respectively physically coupled to the male and the female body portions at a first pair of ends of the first pair of side portions that are opposite the first base. The first channel member may be resilient to permit repeated adjustment of the housing between the closed configuration and the open configuration. The first channel member may include a rigid but resilient metal band. The first channel member may have a first edge and a second edge opposite a length of the first channel member from the first edge, and each of the first pair of ends may have a plurality of teeth along one or both of the first edge and the second edge. The plurality of teeth for each of the first pair of ends may be angled towards the first base. The male body portion and the female body portion may respectively have a first pair of cavities to respectively receive at least the first pair of ends of the first pair of side portions of the first channel member, the first pair of cavities which respectively define a first pair of interior surfaces within the male body portion and the female body portion, and the plurality of teeth for the first pair of ends are respectively physically engaged with the first pair of interior surfaces of the male body portion and the female body portion.

The apparatus may further include at least one transponder received in a transponder receiving cavity of the female body portion or the male body portion, the at least one transponder to wirelessly receive and return signals.

A method to physically couple one or more transponders to a surgical object usable in a surgical environment may be summarized as including positioning a first portion of a surgical object into a first channel formed by a first channel member of an apparatus comprising a housing and the first channel member, the housing comprising a male body portion and a female body portion, the male body portion comprising at least one member that extends from the male body portion, the female body portion comprising at least one slot sized and shaped to fittingly receive the at least one member of the male body portion, the housing adjustable between a closed configuration in which the at least one member of the male body portion is physically engaged with the at least slot of the female body portion and an open configuration in which the at least one member of the male body portion is not physically engaged with the at least slot of the female body portion, the first channel member having a first base and a first pair of side portions that extend from the first base and which are opposed to one another across a width of the first channel member to form the first channel therebetween, the width of the first channel sized to receive at least the first portion of the surgical object therein, the first channel member respectively physically coupled to the male and the female body portions at a first pair of ends of the first pair of side portions that are opposite the first base; and adjusting the housing of the apparatus from the open configuration to the closed configuration to securingly clamp the first portion of the first surgical object in the first channel.

The method may further include adjusting the housing of the apparatus from the closed configuration to the open configuration to unclamp the first portion of the first surgical object from the first channel.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures have not been shown or described in detail to avoid unnecessarily obscuring descriptions of the embodiments. For example, well-known structures associated with transmitters, receivers, or transceivers, and types of surgical instruments have not been shown or described in detail to avoid unnecessarily obscuring descriptions of the embodiments.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed in its broadest sense, that is, as meaning "and/or" unless the context clearly dictates otherwise.

The headings and Abstract of the Disclosure provided herein are for convenience only and do not interpret the scope or meaning of the embodiments.

Figure 1:
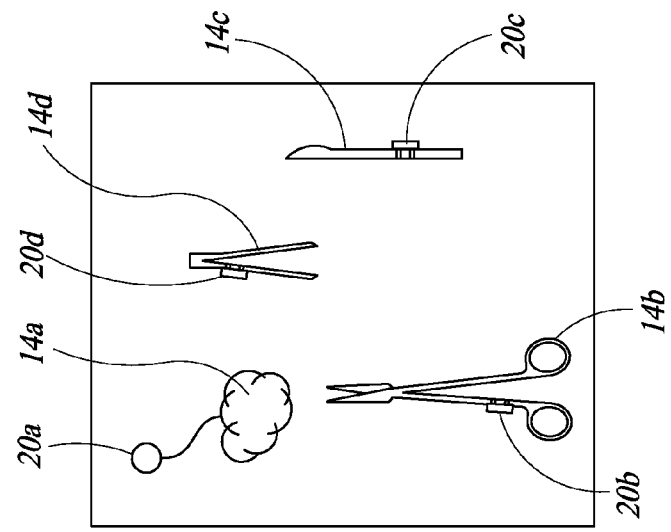
FIG. 1 is a schematic diagram showing a surgical environment illustrating use of an interrogation and detection system to detect one or more objects tagged with a transponder in a patient, according to at least one illustrated embodiment.
Figure 1:
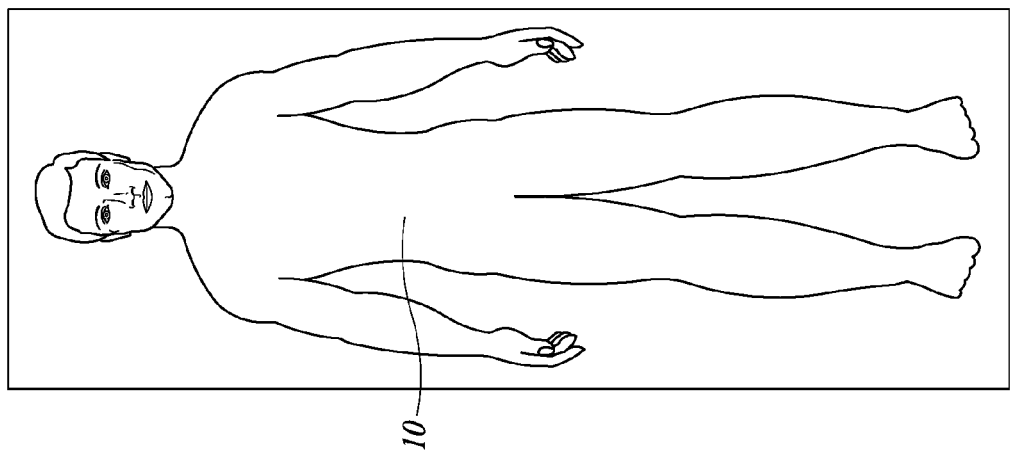
Figure 1:
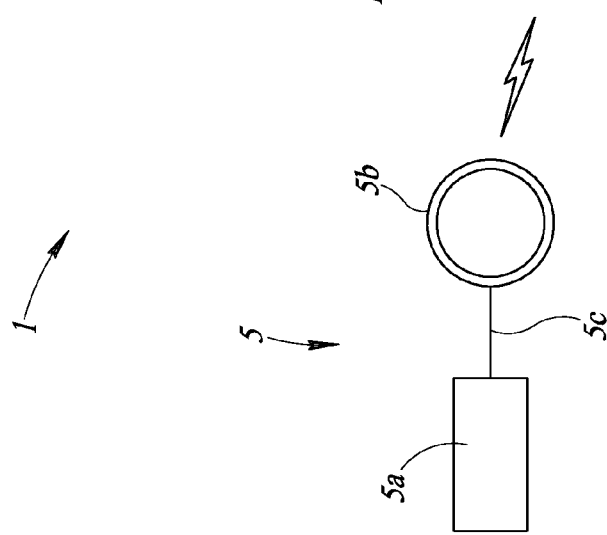

FIG. 1 shows a surgical environment 1 in which a medical provider (not shown) operates an interrogation and detection system 5 to ascertain the presence or absence of objects in, or on, a patient 10.

The interrogation and detection system 5 includes a controller 5a and an antenna 5b. The antenna 5b is coupled to the controller 5a by one or more communication paths, for example a coaxial cable 5c. The antenna 5b may take the form of a hand-held wand. The controller 5a is configured to cause the antenna to emit wireless interrogation signals in one or more wide frequency bands, to receive responses from transponders to such interrogation signals, and to determine the presence, absence, and/or identity of a transponder based on the received responses, if any.

The surgical environment 1 includes a number of surgical objects, collectively 14. Surgical objects 14 may take a variety of forms, for example instruments, accessories and/or disposable objects useful in performing surgical procedures. An apparatus that includes a transponder is attached, affixed, or otherwise coupled to each surgical object 14 (the apparatuses collectively shown as 20). Thus, a respective apparatus 20a-20d is coupled to each of surgical objects 14a-14d.

In some implementations, a transponder is received in a housing of each apparatus 20. For example, the transponder may be molded or potted into the housing and/or may be received in a passageway defined in the housing. The transponder is typically small, as an example approximately 5-10 millimeters long with a diameter of about 1-4 millimeters. Various example transponders will be discussed further herein.

In addition, in at least some implementations, each apparatus 20 advantageously protects the transponder from the ambient environment, for instance from forces, pressure and/or fluids, such as body fluids. In particular, the apparatus 20 withstands and advantageously protects the transponder from various sterilization processes (e.g., autoclaving, electron beam or isotope radiation, ethylene oxide, plasma or corona discharge, and/or liquid sterilants).

Furthermore, in some implementations, each apparatus 20 is substantially non-metallic and spaces the transponder from any metallic portion of the surgical object 14 such that neither the apparatus 20 nor the surgical object 14 interfere with wireless communications between the transponder and the antenna 5b of the interrogation and detection system 5.

In some implementations, each apparatus 20 is both physically coupleable and decoupleable (i.e., removable) with respect to the surgical object 14. Thus, in some implementations, each apparatus 20 is reusable with regard to multiple different surgical objects 14.

Embodiments of the apparatuses 20 disclosed herein may be particularly suited to operate with metallic objects. As used herein, a metallic object, such as surgical objects, may be made partially or wholly of metal, so long as the object could act, alone or in association with other metallic objects, as a Faraday shield or otherwise interfere with communications between the transponders and the interrogation and detection system 5. Examples of various types of metallic objects include, but are not limited to, cutting means (e.g., a scalpel 14c, lancet, knife, scissors), grasping means (e.g., tweezers 14d, forceps), clamping means (e.g., hemostat 14b, clamps), access means (e.g., dilators, specula), injection/irrigation means (e.g., needles, tips), drilling means (e.g., a drill bit), or measurement means (e.g., rulers, calipers).

In addition to the metallic surgical objects, other surgical objects 14 may also be tagged and identified for use with the interrogation and detection system, such as a sponge 14a. In some implementations, the apparatuses 20 of the present disclosure are used to physically couple transponders to such other surgical objects. However, in some implementations, some or all of those surgical objects are tagged using other types of transponder devices or attachment structures.

In use, the medical provider (not shown) may position the antenna 5b proximate the patient 10 in order to detect the presence or absence of the transponder and hence a foreign object. The medical professional may in some embodiments move the antenna 5b along and/or across the body of the patient 10. In some implementations, the antenna 5b is sized to fit at least partially in a body cavity of the patient 10. Although a human patient 10 is illustrated, the described interrogation and detection system 1 may similarly be used on animals.

Furthermore, the present disclosure is not limited to detection and/or identification of surgical objects 14 through interrogation of transponders in a surgical environment 1. Instead, detection and/or identification of surgical objects 14 through interrogation of transponders can be used to track surgical objects 14 through multiple use cycles, sterilization, maintenance, etc., and/or can be used to advantageously detect and/or identify surgical objects 14 within a manufacturing and/or shipping context.

Figure 2:
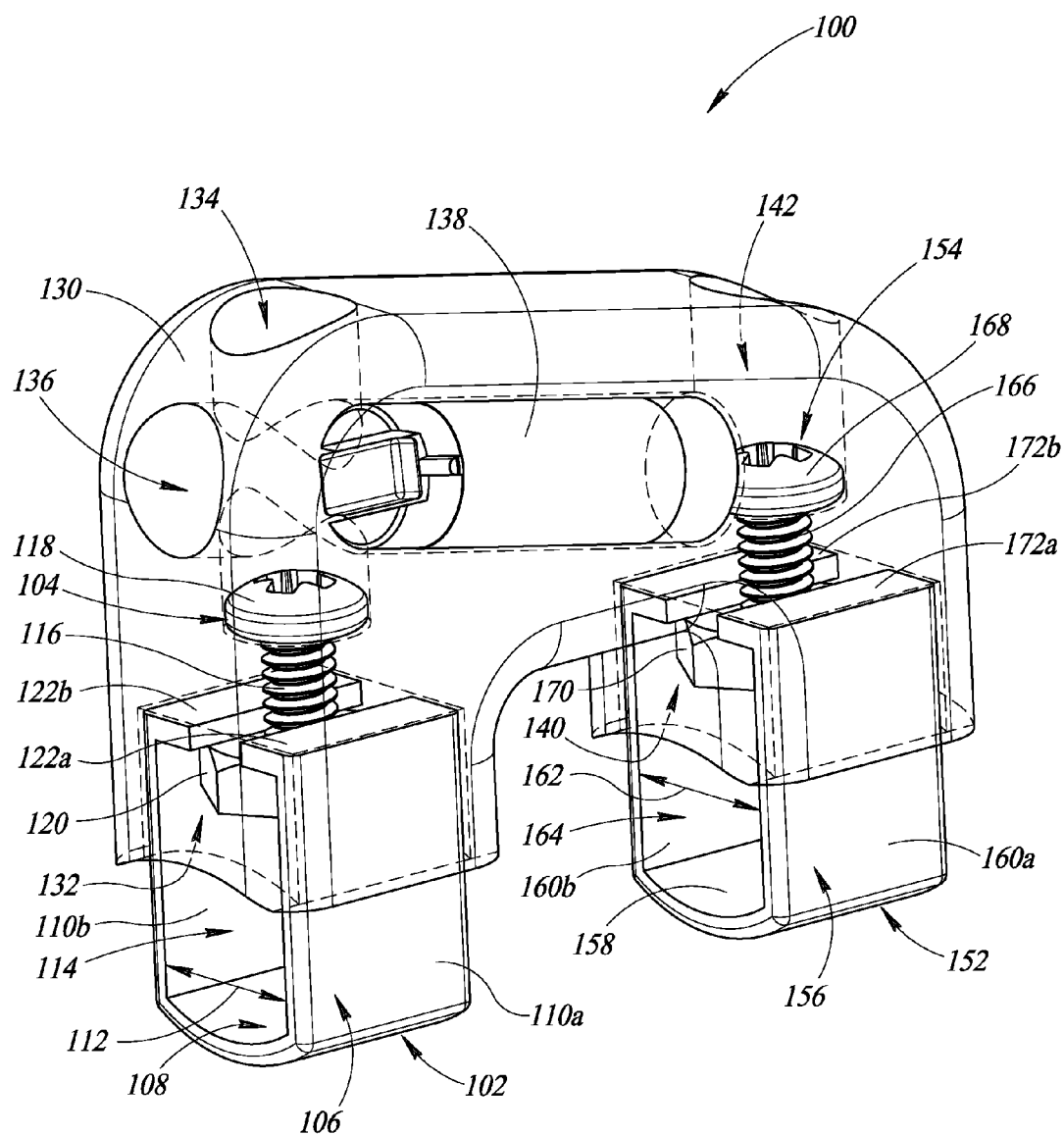
FIG. 2 is an isometric view of an apparatus to physically couple one or more transponders to a surgical object, according to at least one illustrated embodiment.
Figure 3:
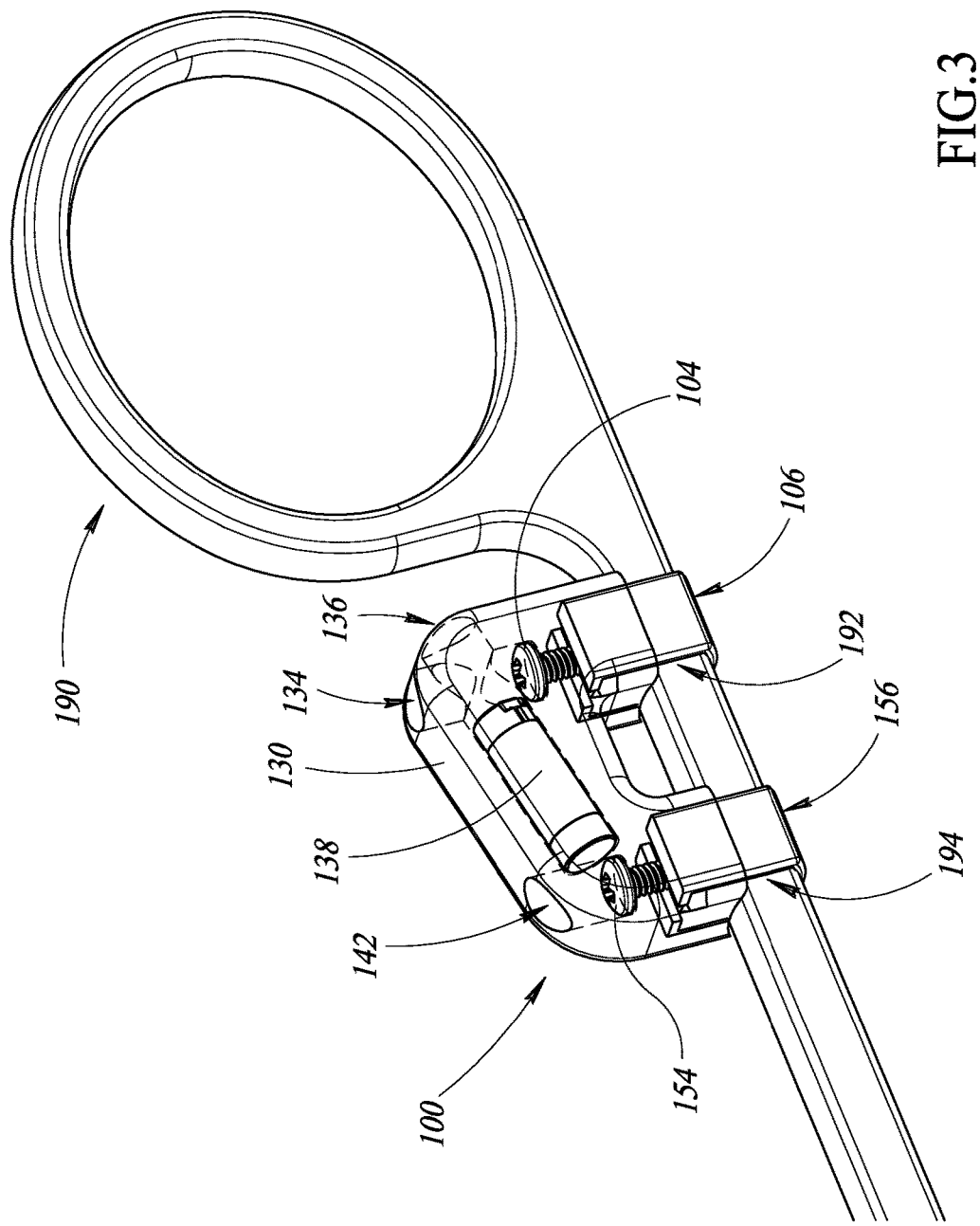
FIG. 3 is an isometric view of the apparatus of FIG. 2 physically coupled to a surgical object, according to at least one illustrated embodiment.
Figure 4:
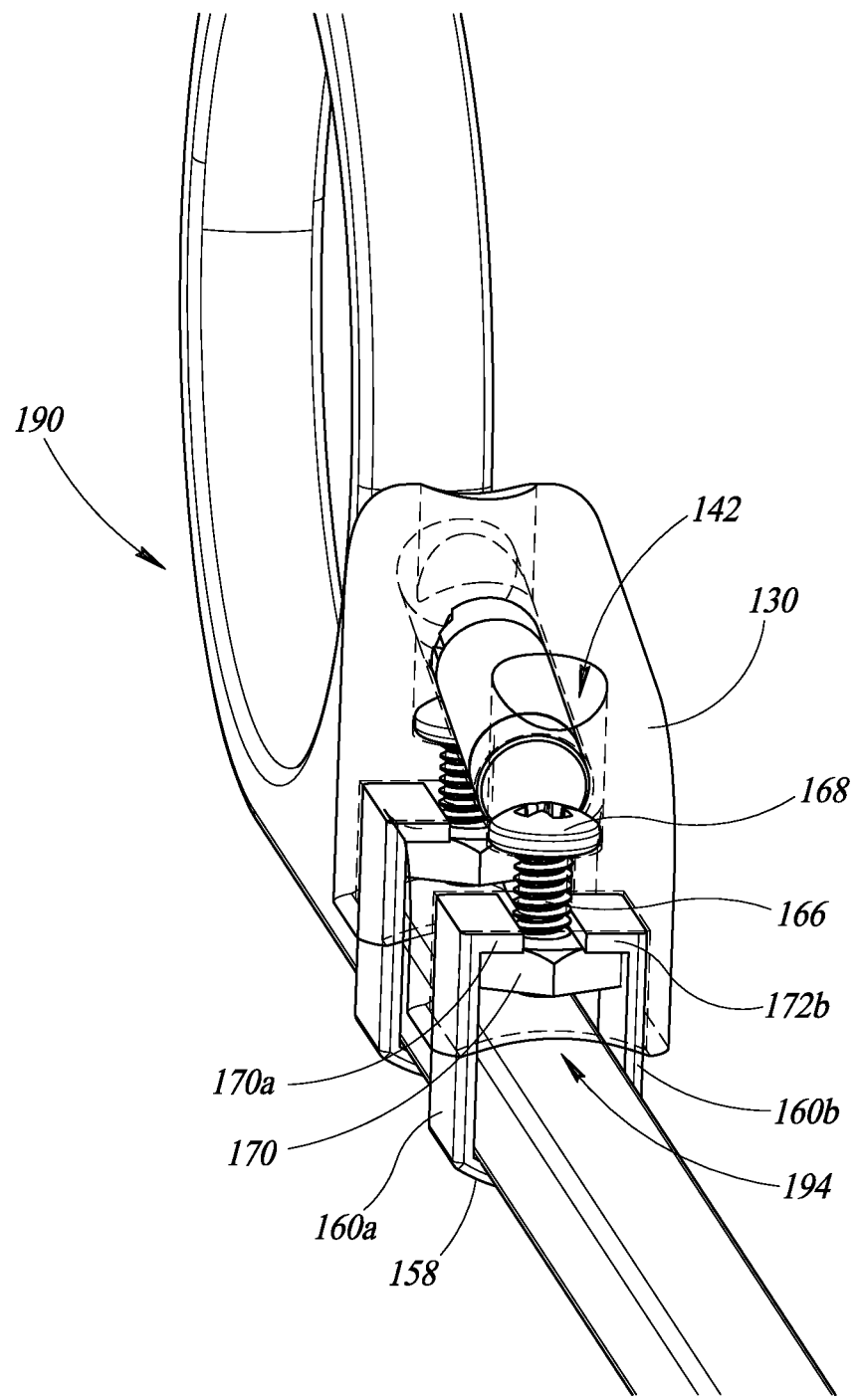
FIG. 4 is an isometric view of the apparatus of FIG. 2 physically coupled to a surgical object, according to at least one illustrated embodiment.

FIGS. 2-4 show an apparatus 100 to physically couple at least one transponder 138 to a surgical object 190. In particular, FIG. 2 shows the apparatus 100 not physically coupled to the surgical object 190 while FIGS. 3 and 4 show the apparatus 100 physically coupled to the surgical object 190.

The apparatus 100 includes a first clamp 102, a second clamp 152, and a housing 130. In each of FIGS. 2-4 the housing 130 is transparently depicted for the purposes of illustrating certain features of the apparatus 100 internal to the housing 130. However, the housing 130 is typically not transparent.

The first clamp 102 includes a first fastener 104 and a first channel member 106. The first channel member 106 has a first base 108 and a first pair of side portions 110a and 110b that extend from the first base 108. The first pair of side portions 110a and 110b are opposed to one another across a width 112 of the first channel member 106 to form a first channel 114 therebetween. The width 112 of the first channel 114 is sized to receive at least a first portion 192 of the surgical object 190 therein.

The first channel member 106 may be metal, plastic, and/or other materials. The first channel member 106 may be a single integral piece or may be formed from multiple components. For example, one or more bending operations may shape a single band of metal into the first channel member 106. Alternatively, the first pair of side portions 110a and 110b may be separate pieces that are physically coupled to the first base 108 (e.g., by welding).

As shown best in FIG. 2, the first base 108 is curved to accommodate a curved surface of the surgical object 190 (e.g., a curved surface of an elongated handle portion or elongated member of the surgical object 190). In some implementations, the first side portions 110a and 110b are similarly curved to accommodate a portion of the surgical object 190 with multiple curved surfaces (e.g., a cylindrical portion). However, in some implementations, neither the first base 108 nor the first side portions 110a and 110b are curved, thereby accommodating a portion of the surgical object 190 with a rectangular cross-section.

Similar to first clamp 102, the second clamp 152 includes a second fastener 154 and a second channel member 156. The second channel member 156 has a second base 158 and a second pair of side portions 160a and 160b that extend from the second base 158. The second pair of side portions 160a and 160b are opposed to one another across a width 162 of the second channel member 156 to form a second channel 164 therebetween. The width 162 of the second channel 164 is sized to receive at least a second portion 194 of the surgical object 190 therein. The second channel member 156 may be constructed as discussed above with respect to the first channel member 106.

The housing 130 has a first cavity 132, a second cavity 140, a first passageway 134, a second passageway 136, and a third passageway 142. The first cavity 132 receives at least a portion of the first pair of side portions 110a and 110b of the first channel member 106. The second cavity 140 receives at least a portion of the second pair of side portions 160a and 160b of the second channel member 156.

The housing 130 may be non-metallic (e.g., formed of one or more plastics) to prevent the housing 130 from impeding or interfering with accurate detection of the transponder 138 by the detection and interrogation system 5. In some implementations, the housing 130 is a single, integral piece of plastic formed through a molding process. For example, the passageways 134, 136, and 142 may be defined within the housing 130 during the molding process. Alternatively, one or more drilling operations may create the passageways 134, 136, and 142 in the single, integral piece of plastic. In other implementations, the housing 130 comprises two or more portions that are secured together after manufacturing. For example, the housing 130 may consist of two body portions that snap together or otherwise have means for coupling to each other (e.g., a complementary peg and hole, clasps, etc.). The housing 130 may be rigid and non-elastic or may exhibit some elasticity.

As shown best in FIG. 2, the first passageway 134 extends in a first direction, the second passageway 136 extends in a second direction, and the third passageway 142 extends in a third direction. The third direction is parallel to the first direction and the second direction is not parallel to the first and the third directions. In some implementations, the second direction is substantially perpendicular to the first and third directions.

The first passageway 134 receives the first fastener 104. The first passageway 134 opens at least in part into the first cavity 132 to permit the first fastener 104 to extend at least in part into the first cavity 132 and adjustably engage with the first channel member 106. In particular, the first fastener 104 includes a first screw that has a head 118 and an elongated shaft 116. The shaft 116 has a first diameter and the head 118 has a second diameter that is greater than the first diameter. The first passageway 134 includes an outer portion that has a third diameter that is greater than the second diameter and an inner portion that has a fourth diameter that is greater than the first diameter and less than the second diameter. As such, the first passageway 134 defines a first shelf at a first transition between the outer portion and the inner portion of the first passageway 134. The head 118 of the first screw engages the first shelf.

The first fastener 104 adjustably engages with the first channel member 106 to securingly clamp the first portion 192 of the surgical object 190 in the first channel 114 of the first channel member 106. More particularly, the shaft 116 has external threading. The first fastener 104 further includes a first nut 120 that securingly receives the shaft 116 (e.g., has internal threading complementary to the external threading of the shaft 116). The first channel member 106 further includes a first pair of flanges 122a and 122b that respectively extend from the first pair of side portions 110a and 110b into the first channel 114. The first nut 120 is positioned between the first pair of flanges 122a and 122b and the first base 108. The first nut 120 physically engages the first pair of flanges 122a and 122b.

Thus, for example, the shaft 116 extends from the first passageway 134 into the first cavity 132 to securingly and adjustably engage with the first nut 120. The first nut 120 physically engages the first pair of flanges 122a and 122b. Rotation of the first screw in a first rotational direction will therefore result in the first clamp 102 being tightened to securingly clamp the first portion 192 of the surgical object 190 in the first channel 114. Likewise, rotation of the first screw in a second rotational direction opposite the first will result in the first clamp 102 being loosened.

The third passageway 142 receives the second fastener 154 and opens at least in part into the second cavity 140 to permit the second fastener 154 to extend at least in part into the second cavity 140 and adjustably engage with the second channel member 156. In particular, the second fastener 154 includes a second screw that has a head 168 and an elongated shaft 166. The shaft 166 has the first diameter and the head 168 has the second diameter that is greater than the second diameter. The second passageway 142 includes an outer portion that has the third diameter that is greater than the second diameter and an inner portion that has the fourth diameter that is greater than the first diameter and less than the second diameter. As such, the second passageway 142 defines a second shelf at a second transition between the outer portion and the inner portion of the second passageway 142. The head 168 of the second screw engages the second shelf.

The second fastener 154 adjustably engages with the second channel member 156 to securingly clamp the second portion 194 of the surgical object 190 in the second channel 164 of the second channel member 156. More particularly, the shaft 166 has external threading and the second fastener 154 further includes a second nut 170 that securingly receives the shaft 166 (e.g., has internal threading complementary to the external threading of the shaft 166). The second channel member 156 further includes a second pair of flanges 172*a* and 172*b* that respectively extend from the second pair of side portions 160*a* and 160*b* into the second channel 164. The second nut 170 is positioned between the second pair of flanges 172*a* and 172*b* and the second base 158. The second nut 170 physically engages the second pair of flanges 172*a* and 172*b*.

Thus, for example, as best shown in FIG. 4, the shaft 166 extends from the second passageway 142 into the second cavity 140 to securingly and adjustably engage with the second nut 170. The second nut 170 physically engages the second pair of flanges 172*a* and 172*b*. Rotation of the second screw in a first rotational direction will therefore result in the second clamp 152 being tightened to securingly clamp the second portion 194 of the surgical object 190 in the second channel 164. Likewise, rotation of the second screw in a second rotational direction opposite the first will result in the second clamp 152 being loosened.

The second passageway 136 receives at least one transponder 138 that wirelessly receives and returns signals. The transponder 138 may be constructed in various manners. For example, the transponder 138 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. In other implementations, the transponder 138 includes an RFID chip that stores identification information that uniquely identifies the transponder 138. Additional details about types of transponders may be found in U.S. Provisional Patent Application No. 60/811,376 filed Jun. 6, 2006; U.S. Provisional Patent Application No. 60/892,028 filed Feb. 28, 2007; and U.S. Provisional Patent Application No. 62/106,052 filed Jan. 21, 2015, each of which are herein incorporated by reference.

The second passageway 136 intersects the first passageway 134. In particular, the second passageway 136 intersects the outer portion of the first passageway 134. The second passageway 136 has a fifth diameter at least greater than the second diameter of the head 118 of the first fastener 104.

In some implementations, an encapsulant (not shown) fills the portions of each of passageways 134, 136, and 142 that are respectively unoccupied by the first fastener 104, the transponder 138, and the second fastener 154. The encapsulant may be shaped to substantially match an exterior surface of the housing 130 and thereby contribute to a substantially continuous exterior surface of the apparatus 100. The encapsulant may ensure that the first fastener 104, the transponder 138, and the second fastener 154 are physically secured in their respective positions and/or prevent contaminants from entering the passageways 134, 136, and 142.

In some implementations, the encapsulant is capable of withstanding multiple rounds of sterilization of the apparatus 100 by one or more of autoclaving, electron beam or isotope radiation, ethylene oxide, plasma or corona discharge, and liquid sterilants. In some implementations, the encapsulant is a biocompatible epoxy. In some implementations, the encapsulant may be readily removed from at least passageways 134 and 142 to permit removal of the apparatus 100 from the surgical object 190. For example, the encapsulant may be removed via drilling or mechanical abrasion.

Furthermore, in some implementations, the apparatus 100 is manufactured and distributed without a transponder 138 attached or received within the housing 130. Advantageously, a transponder 138 compatible with a particular detection and interrogation system can be placed into the apparatus 100 at a subsequent time, for example by the end-user.

Figure 5:
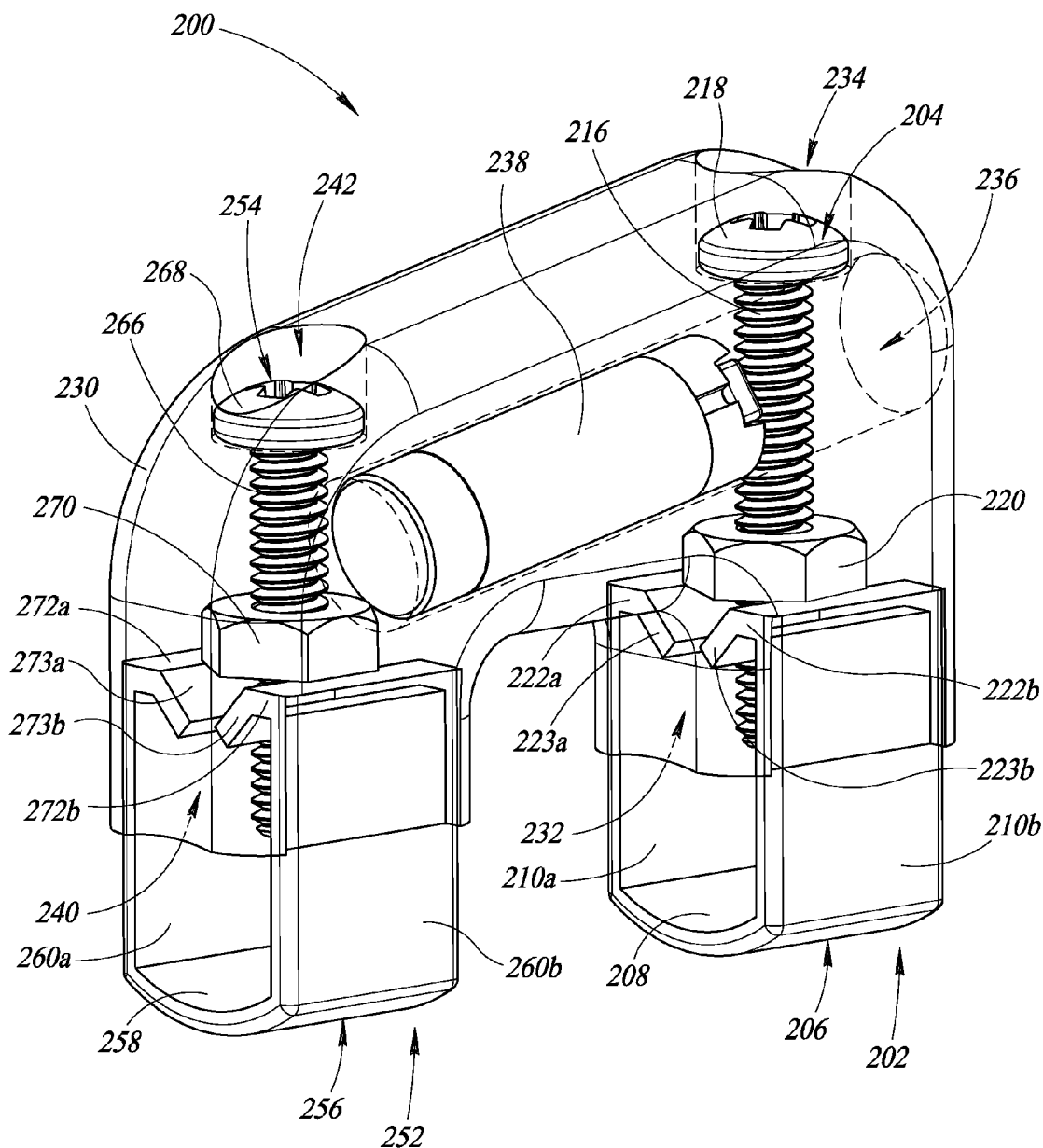
FIG. 5 is an isometric view of an apparatus to physically couple one or more transponders to a surgical object, according to at least one illustrated embodiment.
Figure 6:
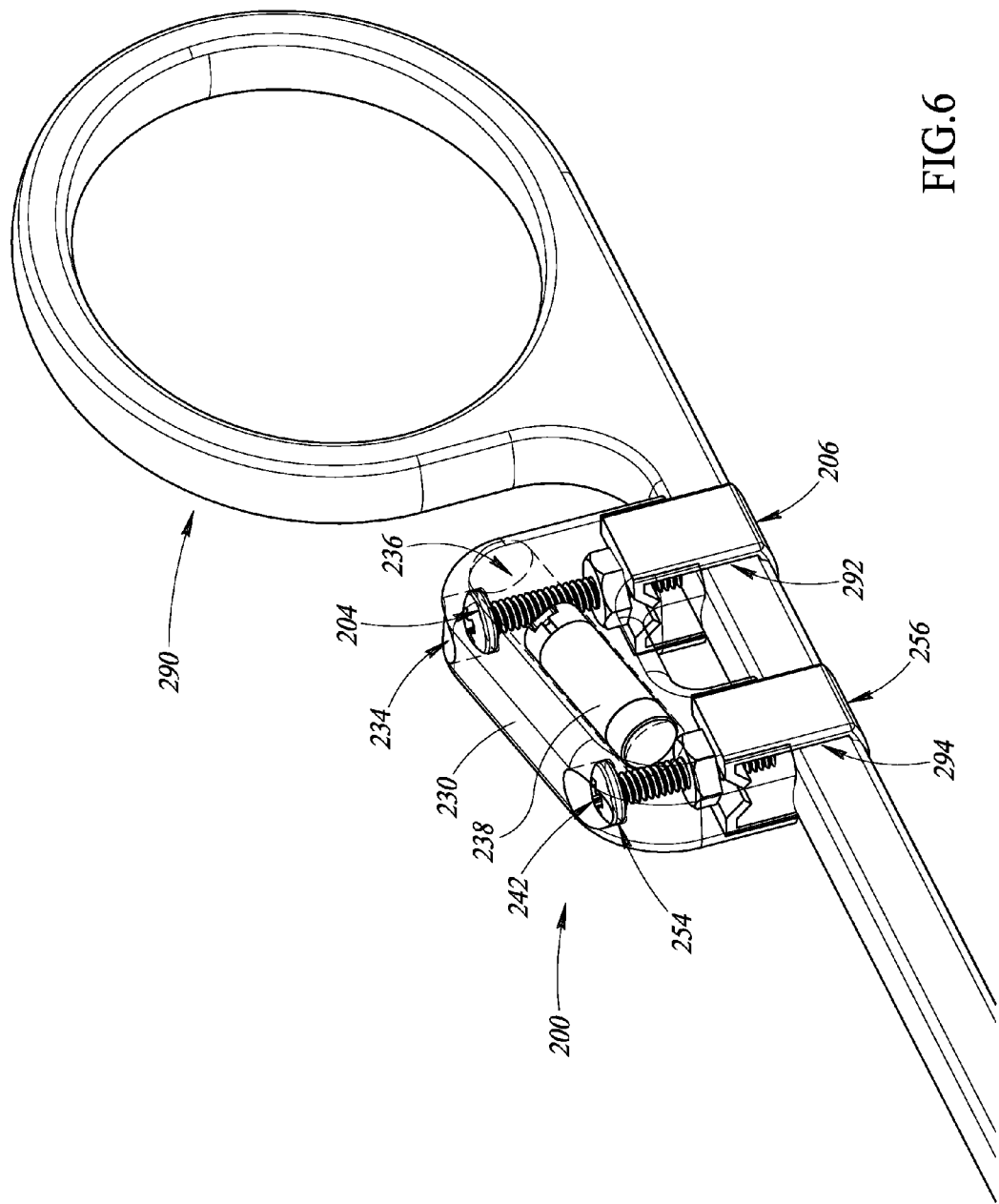
FIG. 6 is an isometric view of the apparatus of FIG. 5 physically coupled to a surgical object, according to at least one illustrated embodiment.
Figure 7:
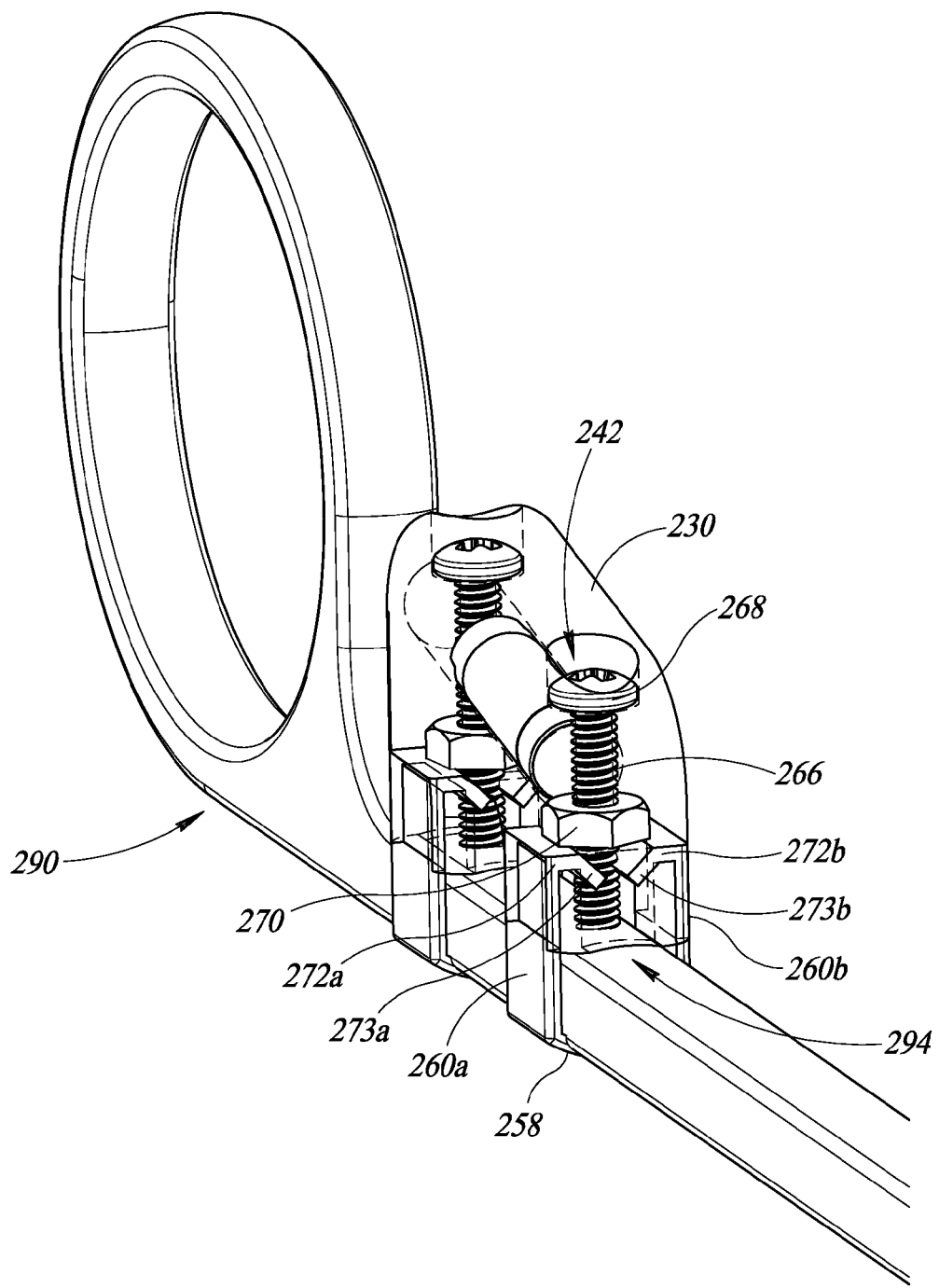
FIG. 7 is an isometric view of the apparatus of FIG. 5 physically coupled to a surgical object, according to at least one illustrated embodiment.
Figure 8:
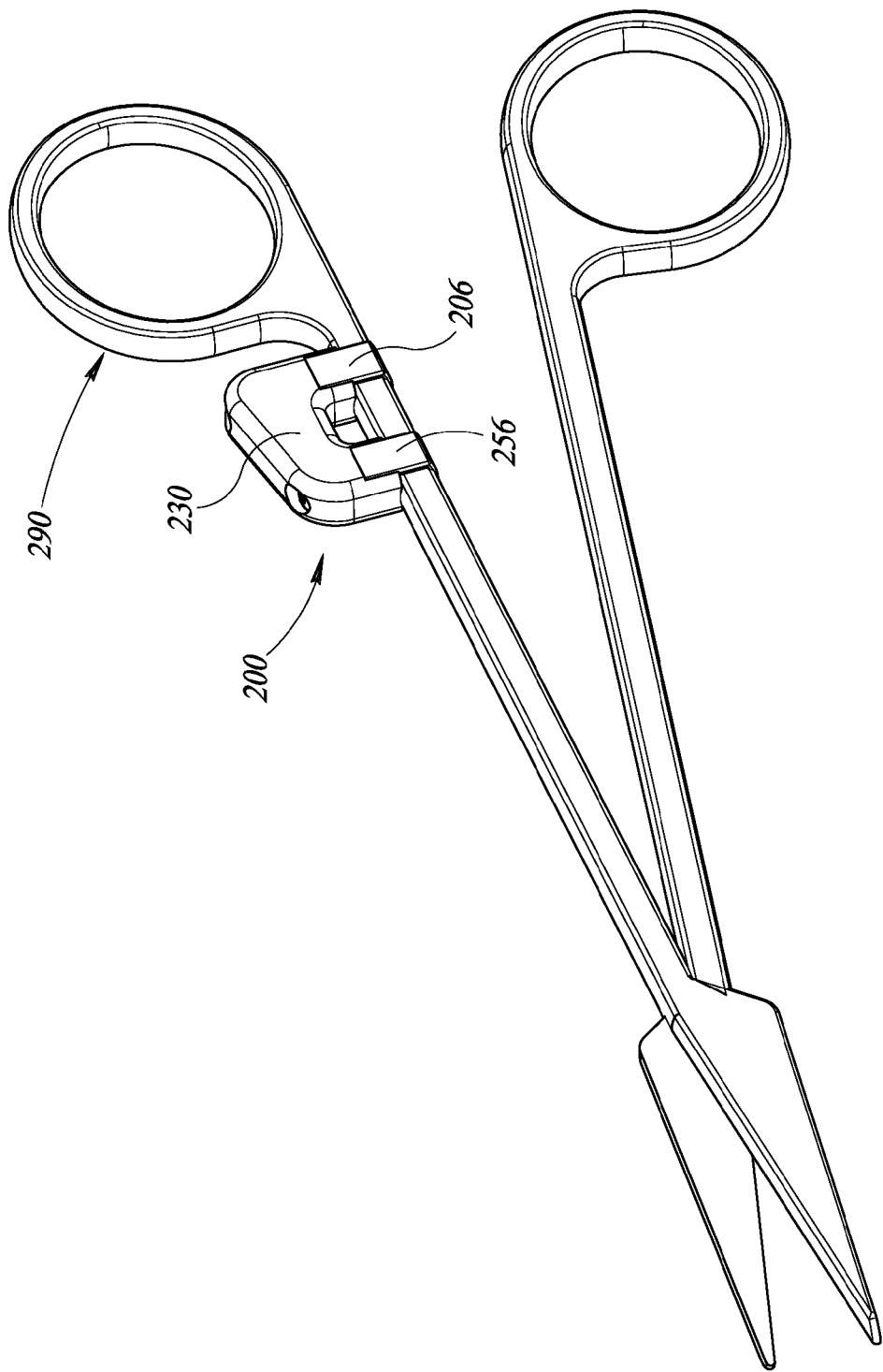
FIG. 8 is an isometric view of the apparatus of FIG. 5 physically coupled to a surgical object, according to at least one illustrated embodiment.

FIGS. 5-8 show an apparatus 200 to physically couple at least one transponder 238 to a surgical object 290. In particular, FIG. 5 shows the apparatus 200 not physically coupled to the surgical object 290 while FIGS. 6-8 show the apparatus 200 physically coupled to the surgical object 290.

The apparatus 200 of FIGS. 5-8 is similar in many respects to the apparatus 100 of FIGS. 2-4, and similar or even identical structures may be identified using analogous reference numbers in the figures. As such, certain commonly shared details regarding the materials and/or structure of apparatuses 100 and 200 are not repeated here in detail to avoid unnecessarily obscuring description of the apparatus 200.

The apparatus 200 includes a first clamp 202, a second clamp 252, and a housing 230. In each of FIGS. 5-7 the housing 230 is transparently depicted for the purposes of illustrating certain features of the apparatus 200 internal to the housing 230. However, the housing 230 is typically not transparent. In FIG. 7, the housing 230 is not transparently depicted.

The first clamp 202 includes a first fastener 204 and a first channel member 206. The first channel member 206 has a first base 208 and a first pair of side portions 210*a* and 210*b* that extend from the first base 208. The first pair of side portions 210*a* and 210*b* are opposed to one another across a width of the first channel member 206 to form a first channel 214 therebetween. The width of the first channel 214 is sized to receive at least a first portion 292 of the surgical object 290 therein.

Similar to first clamp 202, the second clamp 252 includes a second fastener 254 and a second channel member 256. The second channel member 256 has a second base 258 and a second pair of side portions 260*a* and 260*b* that extend from the second base 258. The second pair of side portions 260*a* and 260*b* are opposed to one another across a width of the second channel member 256 to form a second channel 264 therebetween. The width of the second channel 264 is sized to receive at least a second portion 294 of the surgical object 290 therein.

The housing 230 has a first cavity 232, a second cavity 240, a first passageway 234, a second passageway 236, and a third passageway 242. The first cavity 232 receives at least a portion of the first pair of side portions 210*a* and 210*b* of the first channel member 206. The second cavity 240 receives at least a portion of the second pair of side portions 260*a* and 260*b* of the second channel member 256. As best shown in FIG. 8, the cavities 232 and 240 of housing 230 of apparatus 200 may not respectively fully enclose the received portions of the first and the second channel members 206 and 256, as do the cavities 132 and 140 of housing 130 of apparatus 100.

As best shown in FIG. 5, the first passageway 234 receives the first fastener 204. The first passageway 234 opens at least in part into the first cavity 232 to permit the first fastener 204 to extend at least in part into the first cavity 232 and adjustably engage with the first channel member 206. In particular, the first fastener 204 includes a first screw that has a head 218 and an elongated shaft 216. The shaft 216 has a first diameter and the head 218 has a second diameter that is greater than the first diameter. The first passageway 234 includes an outer portion that has a third diameter that is greater than the second diameter and an inner portion that has a fourth diameter that is greater than the first diameter and less than the second diameter. As such, the first passageway 234 defines a first shelf at a first transition between the outer portion and the inner portion of the first passageway 234. The head 218 of the first screw engages the first shelf. In some implementations, the shaft 216 of apparatus 200 is relatively longer than the shaft 116 of apparatus 100.

The first fastener 204 adjustably engages with the first channel member 206 to securingly clamp the first portion 292 of the surgical object 290 in the first channel 214 of the first channel member 206. More particularly, the shaft 216 has external threading. The first fastener 204 further includes a first nut 220 that securingly receives the shaft 216 (e.g., has internal threading complementary to the external threading of the shaft 216). The first channel member 206 further includes a first pair of flanges 222a and 222b that respectively extend from the first pair of side portions 210a and 210b into the first channel 214. The first nut 220 is positioned opposite the first pair of flanges 222a and 222b from the first base 208. The first nut 220 physically engages the first pair of flanges 222a and 222b. In some implementations, the first nut 220 is securely engaged with the first pair of flanges 222a and 222b, for example, by an adhesive or by welding.

Furthermore, the first pair of flanges 222a and 222b include respective end portions 223a and 223b that are respectively angled towards the first base 208 of the first channel member 206. In some implementations, the respective end portions 223a and 223b of the first pair of flanges 222a and 222b securingly engage the external threading of the shaft 216.

Thus, for example, the shaft 216 extends from the first passageway 234 into the first cavity 232 to securingly and adjustably engage with the first nut 220 and/or the respective end portions 223a and 223b of the first pair of flanges 222a and 222b. The first nut 220 may physically engage the first pair of flanges 222a and 222b. Rotation of the first screw in a first rotational direction will therefore result in the first clamp 202 being tightened to securingly clamp the first portion 292 of the surgical object 290 in the first channel 214. Likewise, rotation of the first screw in a second rotational direction opposite the first will result in the first clamp 202 being loosened.

The third passageway 242 receives the second fastener 254 and opens at least in part into the second cavity 240 to permit the second fastener 254 to extend at least in part into the second cavity 240 and adjustably engage with the second channel member 256. In particular, the second fastener 254 includes a second screw that has a head 268 and an elongated shaft 266. The shaft 266 has the first diameter and the head 268 has the second diameter that is greater than the second diameter. The second passageway 242 includes an outer portion that has the third diameter that is greater than the second diameter and an inner portion that has the fourth diameter that is greater than the first diameter and less than the second diameter. As such, the second passageway 242 defines a second shelf at a second transition between the outer portion and the inner portion of the second passageway 242. The head 268 of the second screw engages the second shelf.

The second fastener 254 adjustably engages with the second channel member 256 to securingly clamp the second portion 294 of the surgical object 290 in the second channel 264 of the second channel member 256. More particularly, the shaft 266 has external threading and the second fastener 254 further includes a second nut 270 that securingly receives the shaft 266 (e.g., has internal threading complementary to the external threading of the shaft 266). The second channel member 256 further includes a second pair of flanges 272a and 272b that respectively extend from the second pair of side portions 260a and 260b into the second channel 264. The second nut 270 is positioned opposite the second pair of flanges 272a and 272b from the second base 258. In some implementations, the second nut 270 is securingly engaged with the second pair of flanges 272a and 272b, for example, by an adhesive or by welding.

Furthermore, the second pair of flanges 272a and 272b include respective end portions 273a and 273b that are respectively angled towards the second base 258 of the second channel member 256. In some implementations, the respective end portions 273a and 273b of the second pair of flanges 272a and 272b securingly engage the external threading of the shaft 266.

Thus, for example, as best shown in FIG. 7, the shaft 266 extends from the second passageway 242 into the second cavity 240 to securingly and adjustably engage with the second nut 270 and/or the respective end portions 273a and 273b of the second pair of flanges 272a and 272b. The second nut 270 may physically engage the second pair of flanges 272a and 272b. Rotation of the second screw in a first rotational direction will therefore result in the second clamp 252 being tightened to securingly clamp the second portion 294 of the surgical object 290 in the second channel 264. Likewise, rotation of the second screw in a second rotational direction opposite the first will result in the second clamp 252 being loosened.

In some implementations, the clamps 202 and 252 are respectively tightened until the respective shafts 216 and 256 of fasteners 204 and 254 respectively physically engage the portions 292 and 294 of the surgical object 290 respectively secured in the first and the second channels.

The second passageway 236 receives at least one transponder 238 that wirelessly receives and returns signals. The second passageway 236 intersects the first passageway 234. In particular, the second passageway 236 intersects the inner portion of the first passageway 234. The second passageway 236 has a fifth diameter at least greater than the second diameter of the head 218 of the first fastener 204.

In some implementations, an encapsulant (not shown) fills the portions of each of passageways 234, 236, and 242 that are respectively unoccupied by the first fastener 204, the transponder 238, and the second fastener 254. The encapsulant may be shaped to substantially match an exterior surface of the housing 230 and thereby contribute to a substantially continuous exterior surface of the apparatus 200. The encapsulant may ensure that the first fastener 204, the transponder 238, and the second fastener 254 are physically secured in their respective positions and/or prevent contaminants from entering the passageways 234, 236, and 242.

In some implementations, the encapsulant is capable of withstanding multiple rounds of sterilization of the apparatus 200 by one or more of autoclaving, electron beam or isotope radiation, ethylene oxide, plasma or corona discharge, and liquid sterilants. In some implementations, the encapsulant is a biocompatible epoxy. In some implementations, the encapsulant may be readily removed from at least passageways 234 and 242 to permit removal of the apparatus 200 from the surgical object 290. For example, the encapsulant may be removed via drilling or mechanical abrasion.

Figure 9:
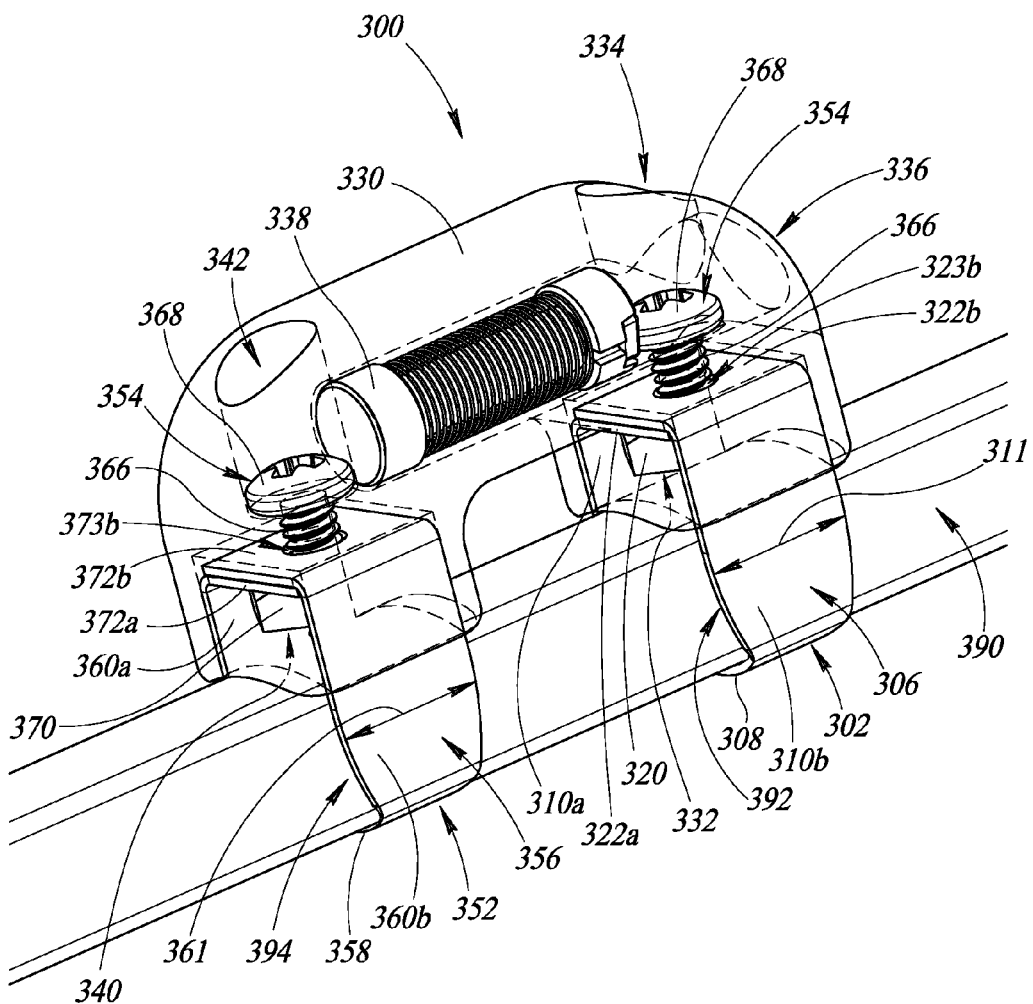
FIG. 9 is an isometric view of an apparatus physically coupled to a surgical object, according to at least one illustrated embodiment.
Figure 10:
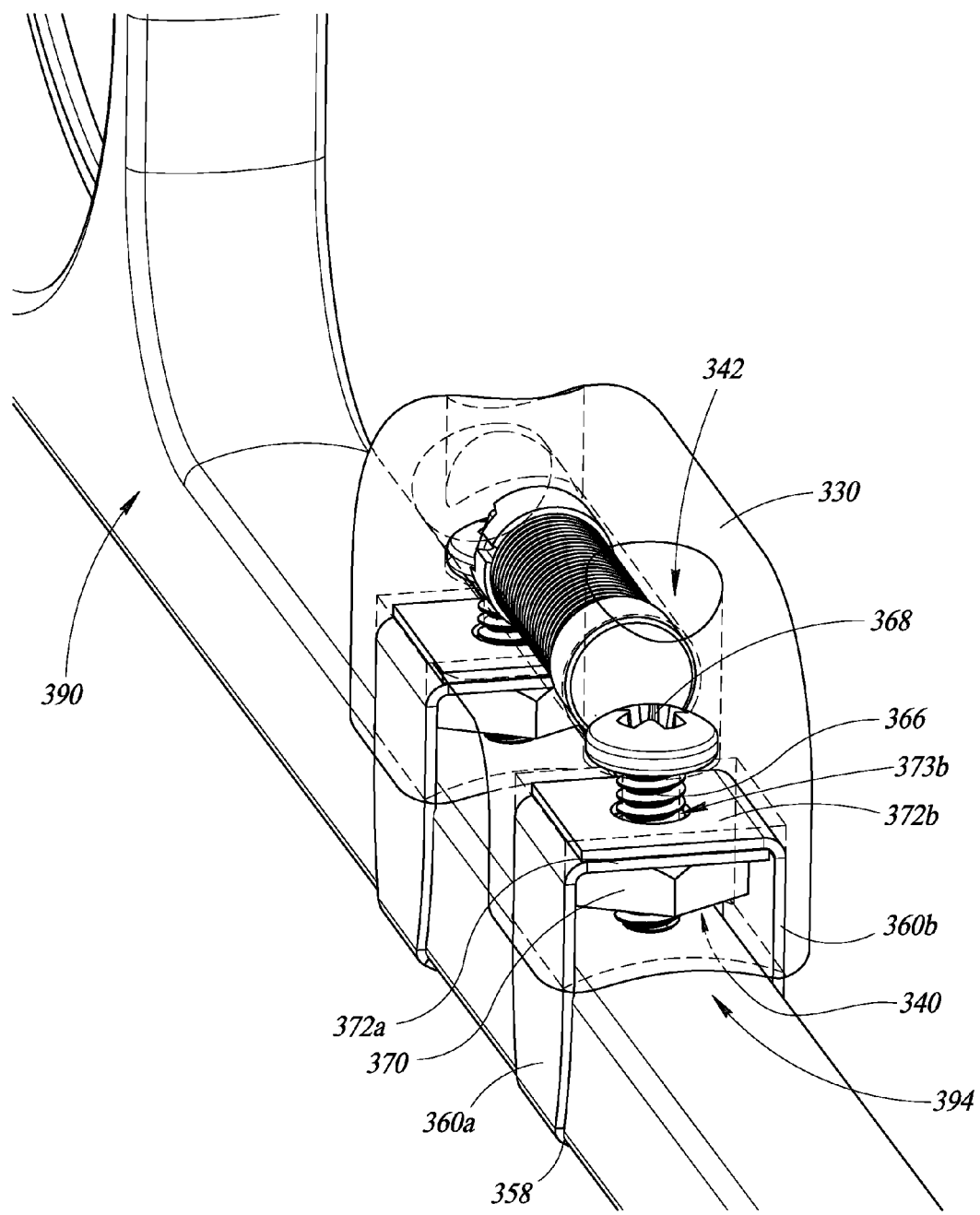
FIG. 10 is an isometric view of the apparatus of FIG. 9 physically coupled to a surgical object, according to at least one illustrated embodiment.

FIGS. 9 and 10 show an apparatus 300 to physically couple at least one transponder 338 to a surgical object 390. The apparatus 300 of FIGS. 9 and 10 is similar in many respects to the apparatus 100 of FIGS. 2-4, and similar or even identical structures may be identified using analogous reference numbers in the figures. As such, certain commonly shared details regarding the materials and/or structure of apparatuses 100 and 300 are not repeated here in detail to avoid unnecessarily obscuring description of the apparatus 300.

The apparatus 300 includes a first clamp 302, a second clamp 352, and a housing 330. In each of FIGS. 9 and 10 the housing 330 is transparently depicted for the purposes of illustrating certain features of the apparatus 300 internal to the housing 330. However, the housing 330 is typically not transparent.

The first clamp 302 includes a first fastener 304 and a first channel member 306. The first channel member 306 has a first base 308 and a first pair of side portions 310a and 310b that extend from the first base 308. The first pair of side portions 310a and 310b are opposed to one another across a width of the first channel member 306 to form a first channel 314 therebetween. The width of the first channel 314 is sized to receive at least a first portion 392 of the surgical object 390 therein. As best shown in FIG. 9, in some implementations, a length 311 of each of the first pair of side portions 310a and 310b may taperedly increase as the respective side portion extends away from the first base 308.

Similar to first clamp 302, the second clamp 352 includes a second fastener 354 and a second channel member 356. The second channel member 356 has a second base 358 and a second pair of side portions 360a and 360b that extend from the second base 358. The second pair of side portions 360a and 360b are opposed to one another across a width of the second channel member 356 to form a second channel 364 therebetween. The width of the second channel 364 is sized to receive at least a second portion 394 of the surgical object 390 therein. As best shown in FIG. 9, in some implementations, a length 361 of each of the second pair of side portions 360a and 360b may taperedly increase as the respective side portion extends away from the second base 358.

The housing 330 has a first cavity 332, a second cavity 340, a first passageway 334, a second passageway 336, and a third passageway 342. The first cavity 332 receives at least a portion of the first pair of side portions 310a and 310b of the first channel member 306. The second cavity 340 receives at least a portion of the second pair of side portions 360a and 360b of the second channel member 356.

The first passageway 334 receives the first fastener 304. The first passageway 334 opens at least in part into the first cavity 332 to permit the first fastener 304 to extend at least in part into the first cavity 332 and adjustably engage with the first channel member 306. In particular, the first fastener 304 includes a first screw that has a head 318 and an elongated shaft 316. The shaft 316 has a first diameter and the head 318 has a second diameter that is greater than the first diameter. The first passageway 334 includes an outer portion that has a third diameter that is greater than the second diameter and an inner portion that has a fourth diameter that is greater than the first diameter and less than the second diameter. As such, the first passageway 334 defines a first shelf at a first transition between the outer portion and the inner portion of the first passageway 334. The head 318 of the first screw engages the first shelf.

The first fastener 304 adjustably engages with the first channel member 306 to securingly clamp the first portion 392 of the surgical object 390 in the first channel 314 of the first channel member 306. More particularly, the shaft 316 may have external threading. The first fastener 304 further includes a first nut 320 that securingly receives the shaft 316 (e.g., has internal threading complementary to the external threading of the shaft 316). The first channel member 306 further includes a first pair of flanges 322a and 322b that respectively extend from the first pair of side portions 310a and 310b into the first channel 314. The first nut 320 is positioned between the first pair of flanges 322a and 322b and the first base 308. The first nut 320 physically engages at least one of the first pair of flanges 322a and 322b.

Furthermore, the first pair of flanges 322a and 322b extend substantially across the entire width of the first channel member 306. The first pair of flanges 322a and 322b overlap and physically engage each other. However, in some implementations, the first pair of flanges 322a and 322b do not physically engage each other.

Each of the first pair of flanges 322a and 322b includes a respective through-hole (only through-hole 323b of flange 322b visible and called out). The respective through-holes of the first pair of flanges 322a and 322b are aligned. The shaft 316 extends through the through-holes of the first pair of flanges 322a and 322b, for example, to reach the first nut 320. In some implementations, the edge of each of the first pair of flanges 322a and 322b that defines the respective through-hole physically engages the exterior threading of the shaft 316.

Thus, for example, the shaft 316 extends from the first passageway 334 into the first cavity 332 to securingly and adjustably engage with the first nut 320 and/or the first pair of flanges 322a and 322b. The first nut 320 physically engages at least one of the first pair of flanges 322a and 322b. Rotation of the first screw in a first rotational direction will therefore result in the first clamp 302 being tightened to securingly clamp the first portion 392 of the surgical object 390 in the first channel 314. Likewise, rotation of the first screw in a second rotational direction opposite the first will result in the first clamp 302 being loosened.

The third passageway 342 receives the second fastener 354 and opens at least in part into the second cavity 340 to permit the second fastener 354 to extend at least in part into the second cavity 340 and adjustably engage with the second channel member 356. In particular, the second fastener 354 includes a second screw that has a head 368 and an elongated shaft 366. The shaft 366 has the first diameter and the head 368 has the second diameter that is greater than the second diameter. The second passageway 342 includes an outer portion that has the third diameter that is greater than the second diameter and an inner portion that has the fourth diameter that is greater than the first diameter and less than the second diameter. As such, the second passageway 342 defines a second shelf at a second transition between the outer portion and the inner portion of the second passageway 342. The head 368 of the second screw engages the second shelf.

The second fastener 354 adjustably engages with the second channel member 356 to securingly clamp the second portion 394 of the surgical object 390 in the second channel 364 of the second channel member 356. More particularly, the shaft 366 has external threading and the second fastener 354 further includes a second nut 370 that securingly receives the shaft 366 (e.g., has internal threading complementary to the external threading of the shaft 366). The second channel member 356 further includes a second pair of flanges 372a and 372b that respectively extend from the second pair of side portions 360a and 360b into the second channel 364. The second nut 370 is positioned between the second pair of flanges 372a and 372b and the second base 358. The second nut 370 physically engages at least one of the second pair of flanges 372a and 372b.

Furthermore, as best shown in FIG. 10, the second pair of flanges 372a and 372b extend substantially across the entire width of the second channel member 356. The second pair of flanges 372a and 372b overlap and physically engage each other. However, in some implementations, the second pair of flanges 372a and 372b do not physically engage each other.

Each of the second pair of flanges 372a and 372b includes a respective through-hole (only through-hole 373b of flange 372b visible and called out). The respective through-holes of the second pair of flanges 372a and 372b are aligned. The shaft 366 extends through the through-holes of the second pair of flanges 372a and 372b, for example, to reach the second nut 370. In some implementations, the edge of the each of the second pair of flanges 372a and 372b that defines the respective through-hole physically engages the exterior threading of the shaft 316.

Thus, for example, as best shown in FIG. 10, the shaft 366 extends from the second passageway 342 into the second cavity 340 to securingly and adjustably engage with the second nut 370 and/or the second pair of flanges 372a and 372b. The second nut 370 physically engages at least one of the second pair of flanges 372a and 372b. Rotation of the second screw in a first rotational direction will therefore result in the second clamp 352 being tightened to securingly clamp the second portion 394 of the surgical object 390 in the second channel 364. Likewise, rotation of the second screw in a second rotational direction opposite the first will result in the second clamp 352 being loosened.

The second passageway 336 receives at least one transponder 338 that wirelessly receives and returns signals. The second passageway 336 intersects the first passageway 334. In particular, the second passageway 336 intersects the outer portion of the first passageway 334. The second passageway 336 has a fifth diameter at least greater than the second diameter of the head 318 of the first fastener 304.

In some implementations, an encapsulant (not shown) fills the portions of each of passageways 334, 336, and 342 that are respectively unoccupied by the first fastener 304, the transponder 338, and the second fastener 354. The encapsulant may be shaped to substantially match an exterior surface of the housing 330 and thereby contribute to a substantially continuous exterior surface of the apparatus 300. The encapsulant may ensure that the first fastener 304, the transponder 338, and the second fastener 354 are physically secured in their respective positions and/or prevent contaminants from entering the passageways 334, 336, and 342.

In some implementations, the encapsulant is capable of withstanding multiple rounds of sterilization of the apparatus 300 by one or more of autoclaving, electron beam or isotope radiation, ethylene oxide, plasma or corona discharge, and liquid sterilants. In some implementations, the encapsulant is a biocompatible epoxy. In some implementations, the encapsulant may be readily removed from at least passageways 334 and 342 to permit removal of the apparatus 300 from the surgical object 390. For example, the encapsulant may be removed via drilling or mechanical abrasion.

Figure 11:
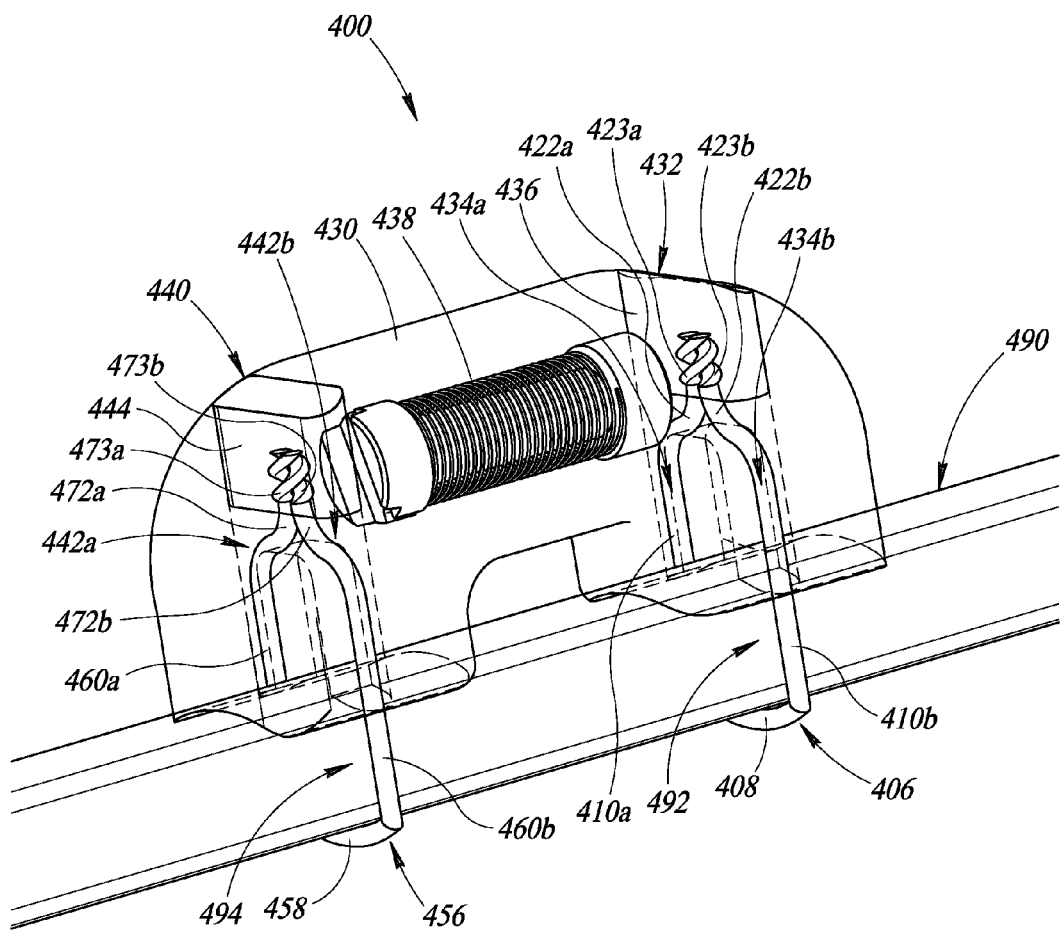
FIG. 11 is an isometric view of an apparatus physically coupled to a surgical object, according to at least one illustrated embodiment.
Figure 12:
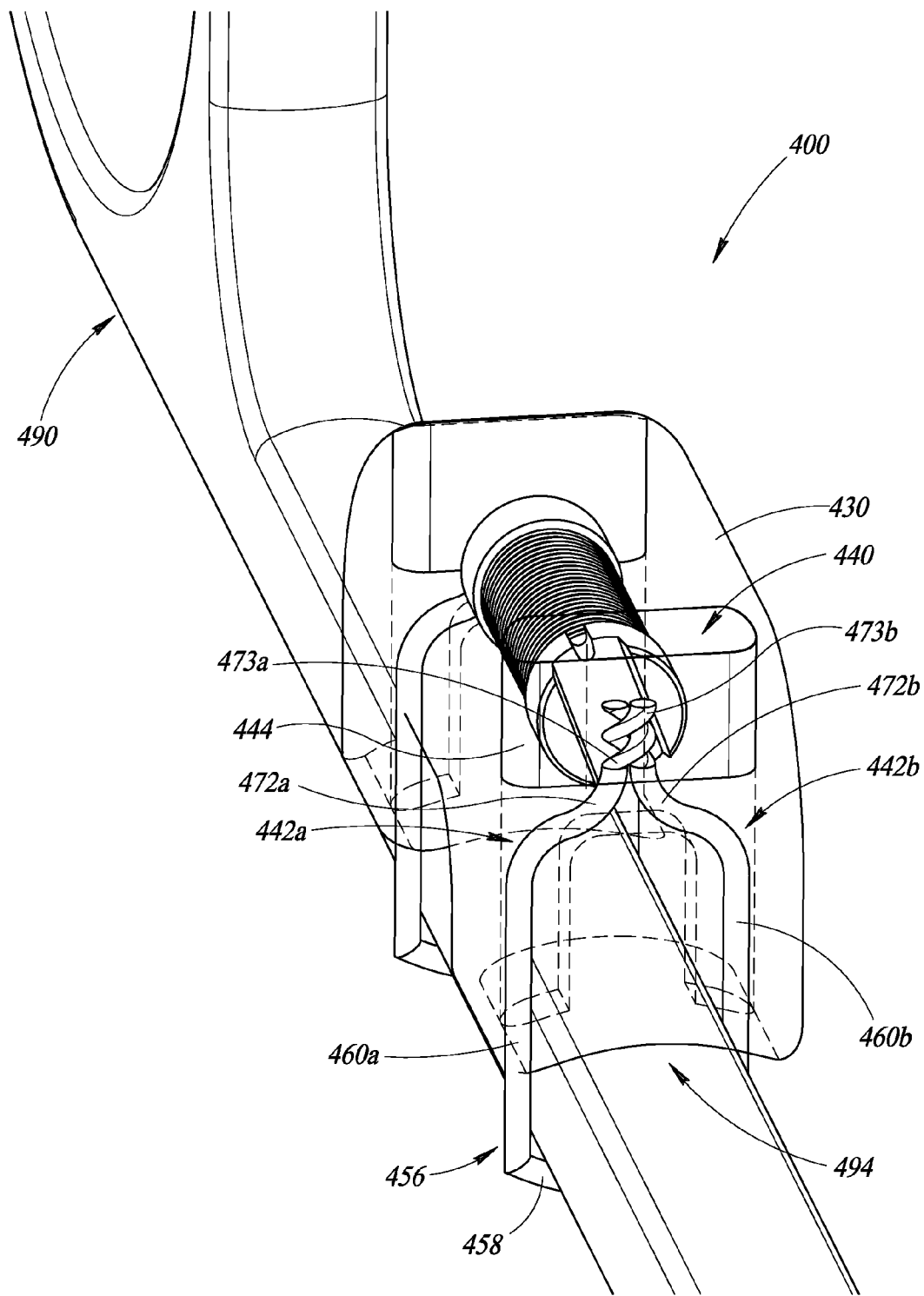
FIG. 12 is an isometric view of the apparatus of FIG. 11 physically coupled to a surgical object, according to at least one illustrated embodiment.

FIGS. 11 and 12 show an apparatus 400 to physically couple at least one transponder 438 to a surgical object 490. The apparatus 400 of FIGS. 11 and 12 is similar in many respects to the apparatus 100 of FIGS. 2-4, and similar or even identical structures may be identified using analogous reference numbers in the figures. As such, certain commonly shared details regarding the materials and/or structure of apparatuses 100 and 400 are not repeated here in detail to avoid unnecessarily obscuring description of the apparatus 400.

The apparatus 400 includes a first channel member 406, a second channel member 456, and a housing 430. In each of FIGS. 11 and 12 the housing 430 is transparently depicted for the purposes of illustrating certain features of the apparatus 400 internal to the housing 430. However, the housing 430 is typically not transparent.

The first channel member 406 has a first base 408 and a first pair of side portions 410a and 410b that extend from the first base 408. The first pair of side portions 410a and 410b are opposed to one another across a width of the first channel member 406 to form a first channel 414 therebetween. The width of the first channel 414 is sized to receive at least a first portion 492 of the surgical object 490 therein. In some implementations, the first base 408 and the first pair of side portions 461a and 410b are cylindrical. For example, the first channel member 406 may be formed from a wire.

Similar to first channel member 406, the second channel member 456 has a second base 458 and a second pair of side portions 460a and 460b that extend from the second base 458. The second pair of side portions 460a and 460b are opposed to one another across a width of the second channel member 456 to form a second channel 464 therebetween. The width of the second channel 464 is sized to receive at least a second portion 494 of the surgical object 490 therein. In some implementations, the second base 458 and the second pair of side portions 460a and 460b are cylindrical.

The housing 430 has a first cavity 432 and a second cavity 440. The first cavity 432 has a first body portion 436 and a first pair of leg portions 434a and 434b that respectively extend from the first body portion 436 in a first direction. Likewise, the second cavity 440 has a second body portion 444 and a second pair of leg portions 442a and 442b that respectively extend from the second body portion 444 in the first direction.

The first pair of side portions 410a and 410b respectively extend through the first pair of leg portions 434a and 434b to reach the first body portion 436 of the first cavity 432. The first pair of side portions 410a and 410b are physically secured to each other within the first body portion 436 of the first cavity 432 to physically secure the first channel member 406 with respect to the housing 430 and clamp the first portion 492 of the surgical object 490 in the first channel.

More particularly, in some implementations, the first pair of side portions 410a and 410b are twisted together in the first body portion 436 of the first cavity 432. For example, the first pair of side portions 410a and 410b may respectively have a first pair of end portions 422a and 422b that respectively extend from the first pair of side portions 410a and 410b into the first channel. The first pair of end portions 422a and 422b may respectively have a first pair of complementary helical structures 423a and 423b that physically engage each other.

As best shown in FIG. 12, the second pair of side portions 460*a* and 460*b* respectively extend through the second pair of leg portions 442*a* and 442*b* to reach the second body portion 444 of the second cavity 440. The second pair of side portions 460*a* and 460*b* are physically secured to each other within the second body portion 444 of the second cavity 440 to physically secure the second channel member 456 with respect to the housing 430 and clamp the second portion 494 of the surgical object 490 in the second channel.

More particularly, in some implementations, the second pair of side portions 460*a* and 460*b* are twisted together in the second body portion 444 of the second cavity 440. For example, the second pair of side portions 460*a* and 460*b* may respectively have a second pair of end portions 472*a* and 472*b* that respectively extend from the second pair of side portions 460*a* and 460*b* into the second channel. The second pair of end portions 472*a* and 472*b* may respectively have a second pair of complementary helical structures 473*a* and 473*b* that physically engage each other.

At least one transponder 438 may be received in the housing 430. For example, the housing 430 may include one or more passageways to receive the at least one transponder 438. In implementations in which the at least one transponder 438 is received in a passageway of the housing 130, an encapsulant (not shown) fills the portion of such passageway that is unoccupied by the at least one transponder 438. The encapsulant may be a biocompatible epoxy.

In other implementations, the at least one transponder 438 is molded or potted into the housing 430. For example, the at least one transponder 438 may be molded into the housing 430 when the housing 430 initially created through a molding process. As another example, the housing 430 may include one or more transponder receiving cavities (not shown) and the at least one transponder 438 may be potted into such a transponder receiving cavity by an end-user (e.g., using an encapsulant). In yet other implementations, the at least one transponder 438 may be free-floating within such a transponder receiving cavity.

Figure 13:
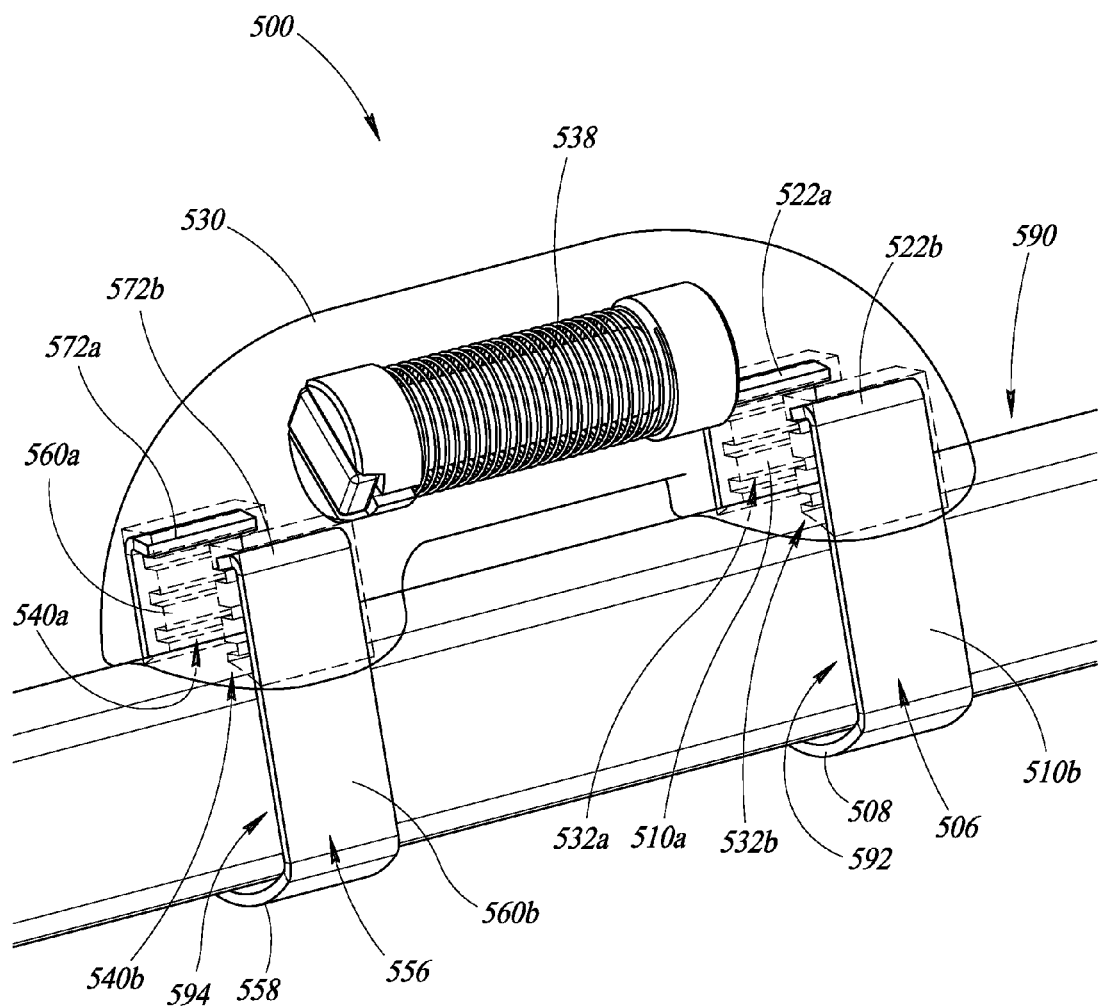
FIG. 13 is an isometric view of an apparatus physically coupled to a surgical object, according to at least one illustrated embodiment.
Figure 14:
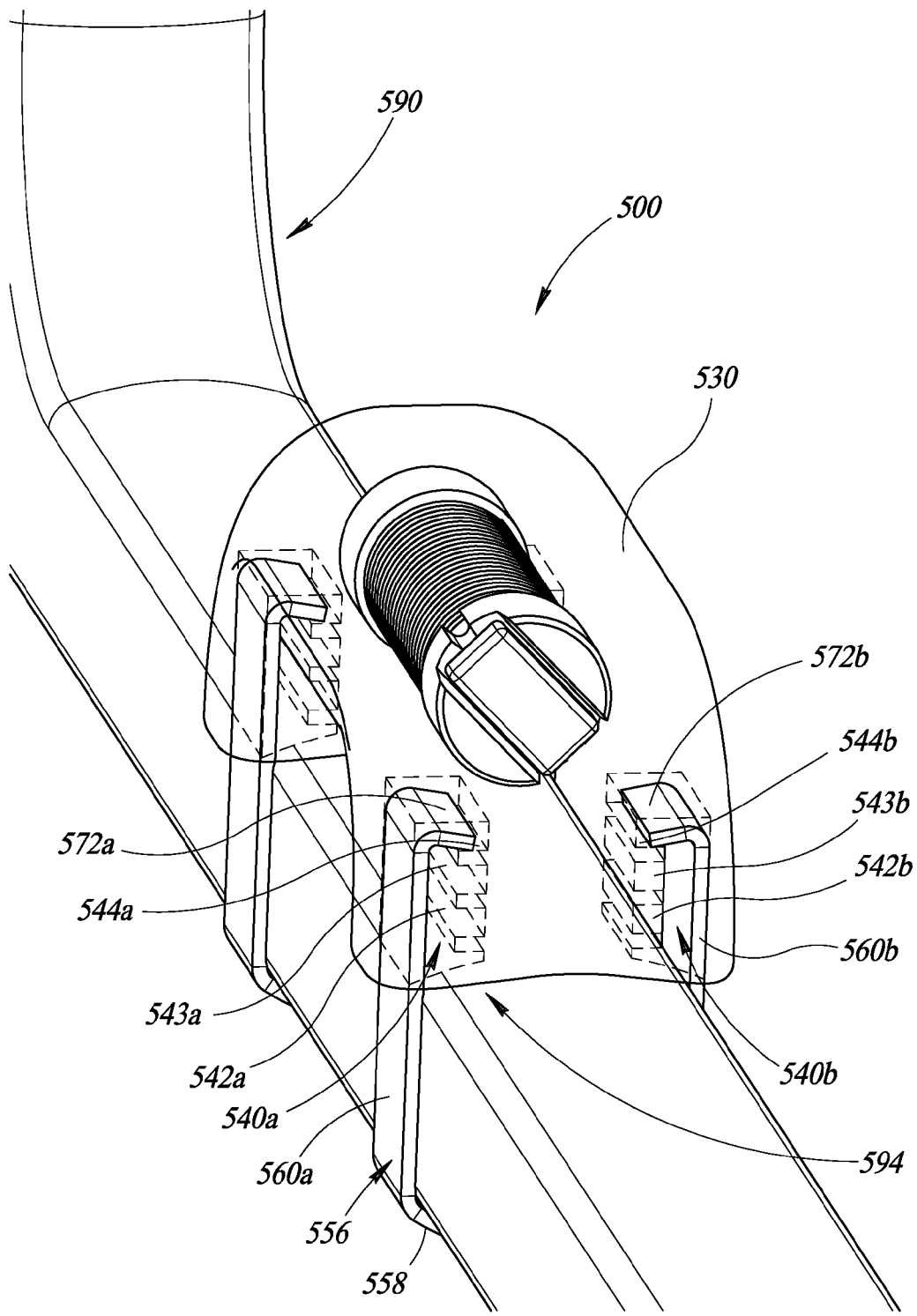
FIG. 14 is an isometric view of the apparatus of FIG. 13 physically coupled to a surgical object, according to at least one illustrated embodiment.

FIGS. 13 and 14 show an apparatus 500 to physically couple at least one transponder 538 to a surgical object 590. The apparatus 500 of FIGS. 13 and 14 is similar in many respects to the apparatus 100 of FIGS. 2-4, and similar or even identical structures may be identified using analogous reference numbers in the figures. As such, certain commonly shared details regarding the materials and/or structure of apparatuses 100 and 500 are not repeated here in detail to avoid unnecessarily obscuring description of the apparatus 500.

The apparatus 500 includes a first channel member 506, a second channel member 556, and a housing 530. In each of FIGS. 13 and 14 the housing 530 is transparently depicted for the purposes of illustrating certain features of the apparatus 500 internal to the housing 530. However, the housing 530 is typically not transparent.

The first channel member 506 has a first base 508 and a first pair of side portions 510*a* and 510*b* that extend from the first base 508. The first pair of side portions 510*a* and 510*b* are opposed to one another across a width of the first channel member 506 to form a first channel 514 therebetween. The width of the first channel 514 is sized to receive at least a first portion 592 of the surgical object 590 therein. The first channel member 506 further has a first pair of flanges 522*a* and 522*b* that respectively extend from the first pair of side portions 510*a* and 510*b* into the first channel. In some implementations, the first pair of flanges 522*a* and 522*b* are respectively angled slightly downwards towards the first base 508. In other implementations, the first pair of flanges 522*a* and 522*b* respectively extend perpendicular to the first pair of side portions 510*a* and 510*b*.

Similar to first channel member 506, the second channel member 556 has a second base 558 and a second pair of side portions 560*a* and 560*b* that extend from the second base 558. The second pair of side portions 560*a* and 560*b* are opposed to one another across a width of the second channel member 556 to form a second channel 564 therebetween. The width of the second channel 564 is sized to receive at least a second portion 594 of the surgical object 590 therein. As best shown in FIG. 14, the second channel member 556 further has a second pair of flanges 572*a* and 572*b* that respectively extend from the second pair of side portions 560*a* and 560*b* into the second channel. In some implementations, the second pair of flanges 572*a* and 572*b* are respectively angled slightly downwards towards the second base 558. In other implementations, the second pair of flanges 572*a* and 572*b* respectively extend perpendicular to the second pair of side portions 560*a* and 560*b*.

The housing 530 has a first pair of cavities 532*a* and 532*b* and a second pair of cavities 540*a* and 540*b*. The first pair of cavities 532*a* and 532*b* respectively receive at least the first pair of flanges 522*a* and 522*b* of the first channel member 506. Likewise, the second pair of cavities 540*a* and 540*b* respectively receive at least the second pair of flanges 572*a* and 572*b* of the second channel member 556.

A plurality of pairs of teeth are respectively defined in each of the first pair of cavities 532*a* and 532*b* and the second pair of cavities 540*a* and 540*b* (only certain pairs of teeth numerically called out to prevent obscuring the drawings). The flanges of each channel member 506 and 556 physically engage with a respective pair of the plurality of pairs of teeth to respectively physically secure the channel members 506 and 556 with respect to the housing 530.

As an example, as best shown in FIG. 14, a first pair of teeth 542*a* and 542*b*, a second pair of teeth 543*a* and 543*b*, and a third pair of teeth 544*a* and 544*b* are respectively defined in the second pair of cavities 540*a* and 540*b*. Each tooth extends from the housing 530 into the corresponding cavity. The second pair of flanges 572*a* and 572*b* of the second channel member 556 are respectively physically engaged with the third pair of teeth 544*a* and 544*b* to physically secure the second channel member 556 with respect to the housing 530 and securingly clamp the second portion 594 of the surgical object 590 into the second channel of the second channel member 556.

According to an aspect of the present disclosure, the plurality of pairs of teeth are located at a plurality of different positions that respectively correspond to a plurality of different potential channel heights for the channel defined by the corresponding channel member. Such may advantageously allow snug coupling of the apparatus 500 to different surgical objects 590 having different heights or thicknesses. As an example, as shown in FIG. 14, the second pair of flanges 572*a* and 572*b* of the second channel member 556 are respectively physically engaged with the third pair of teeth 544*a* and 544*b*. This configuration results in the smallest available channel height (e.g., distance from second base 558 to the housing 530). Adjusting the second channel member 556 such that the second pair of flanges 572*a* and 572*b* respectively physically engage a different pair of teeth (e.g., the first pair of teeth 542*a* and 542*b*) results in a relatively larger channel height that may accommodate a relatively larger portion of the same or different surgical object. Further, although three pairs of teeth are shown in each pair of cavities in FIG. 14, any number of teeth may be defined in the pairs of cavities.

At least one transponder 538 may be received in the housing 530. For example, the housing 530 may include one or more passageways to receive the at least one transponder 538. In implementations in which the at least one transponder 538 is received in a passageway of the housing 130, an encapsulant (not shown) fills the portion of such passageway that is unoccupied by the at least one transponder 538. The encapsulant may be a biocompatible epoxy.

In other implementations, the at least one transponder 538 is molded or potted into the housing 530. For example, the at least one transponder 538 may be molded into the housing 530 when the housing 530 initially created through a molding process. As another example, the housing 530 may include one or more transponder receiving cavities (not shown) and the at least one transponder 538 may be potted into such a transponder receiving cavity by an end-user (e.g., using an encapsulant). In yet other implementations, the at least one transponder 538 may be free-floating within such a transponder receiving cavity.

Figure 15:
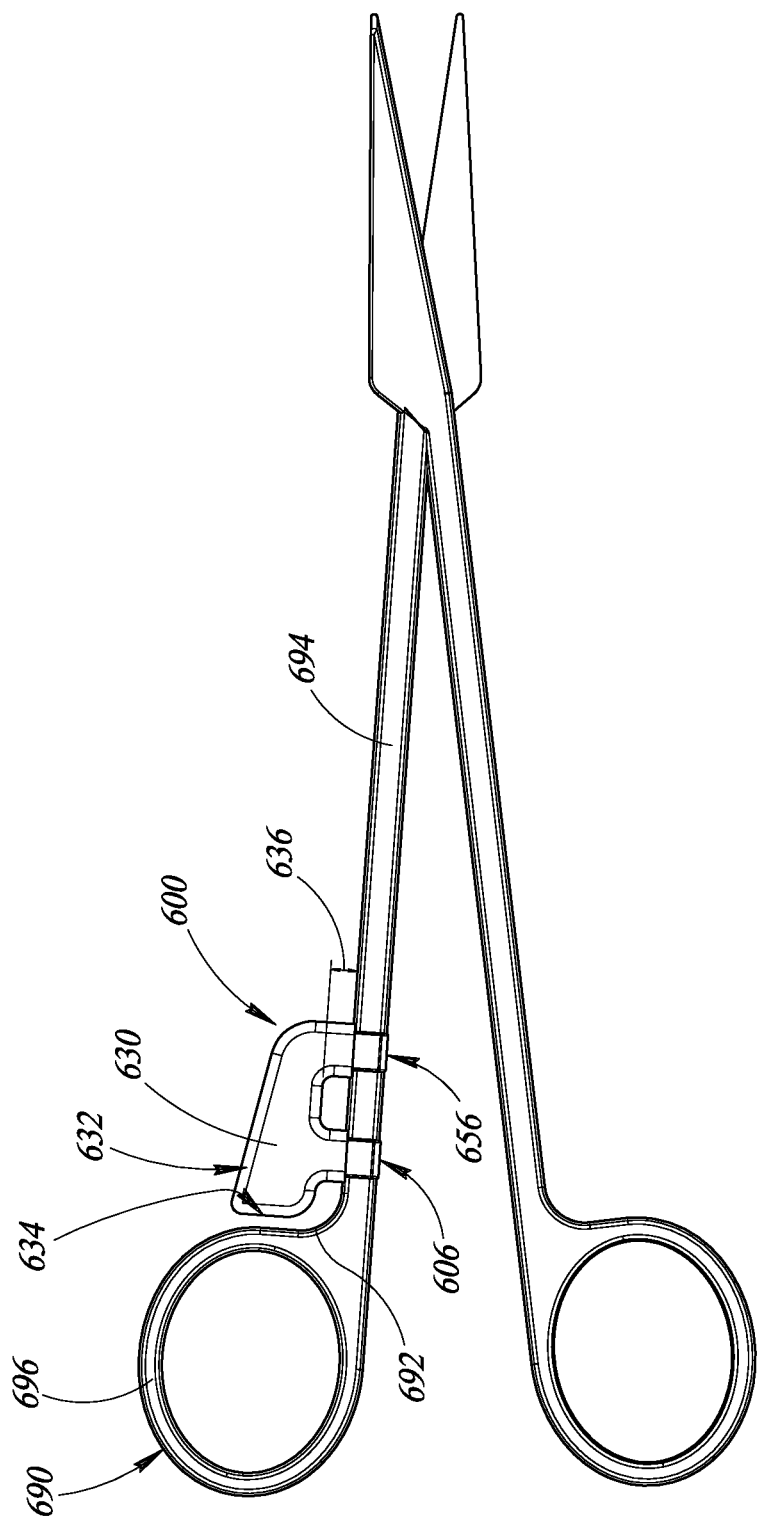
FIG. 15 is a side elevational view of an apparatus physically coupled to a surgical object, according to at least one illustrated embodiment.

FIG. 15 is a side elevational view of an apparatus 600 physically coupled to a surgical object 690, according to at least one illustrated embodiment. The apparatus 600 of FIG. 15 is similar in many respects to the apparatus 100 of FIGS. 2-4, and similar or even identical structures may be identified using analogous reference numbers in the figures. As such, certain commonly shared details regarding the materials and/or structure of apparatuses 100 and 600 are not repeated here in detail to avoid unnecessarily obscuring description of the apparatus 600.

The apparatus includes a first channel member 606, a second channel member 656, and a housing 630. The first channel member 606 and the second channel member 656 are respectively physically secured with respect to the housing 632 securingly clamp respective portions of the surgical object 690 in a first channel and a second channel respectively defined thereby. The housing 630 receives at least one transponder.

In particular, FIG. 15 illustrates various spatial features of the apparatus 600. For example, as shown in FIG. 15, the housing 630 is substantially spaced a distance 636 from the surgical object 690. Such spacing distance 636 may advantageously help to prevent signal loss due to any metallic portions of the surgical object 690 acting as a Faraday shield or otherwise interfering with wireless communications of the transponder.

An exterior profile of the housing 630 includes a first exterior surface 632 and a second exterior surface 634. The first exterior surface 632 extends perpendicularly away from an elongated member 694 of the surgical object 690 and then curves and extends towards a finger loop 696 of the surgical object 690. The second exterior surface 634 extends from the first exterior surface 632 towards the elongated member 694 and includes an arcuate portion that substantially matches an arcuate surface 692 of the surgical object 690. The arcuate surface 692 is a transition between the finger loop 696 and the elongated member 694.

Figure 16:
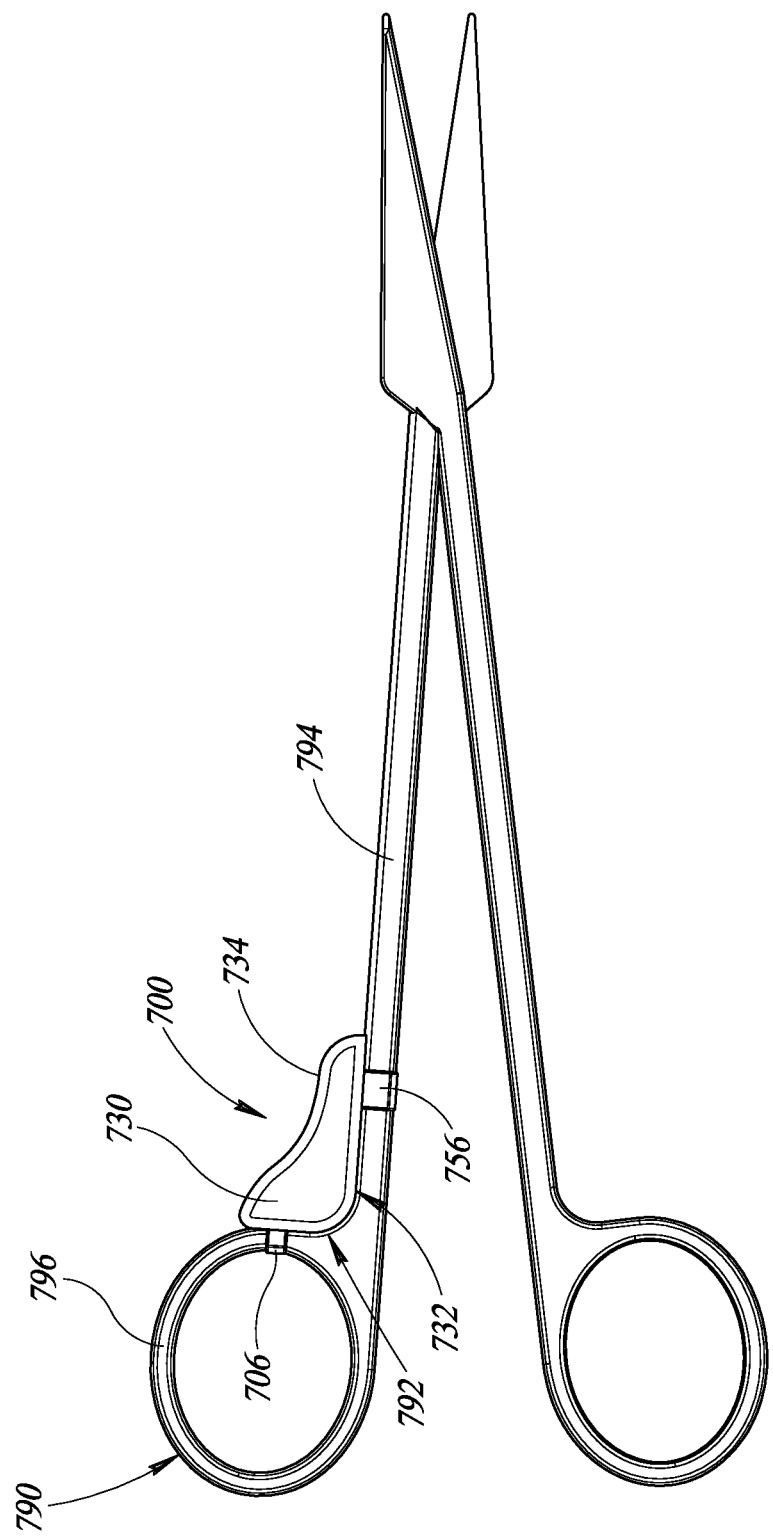
FIG. 16 is a side elevational view of an apparatus physically coupled to a surgical object, according to at least one illustrated embodiment.
Figure 17:
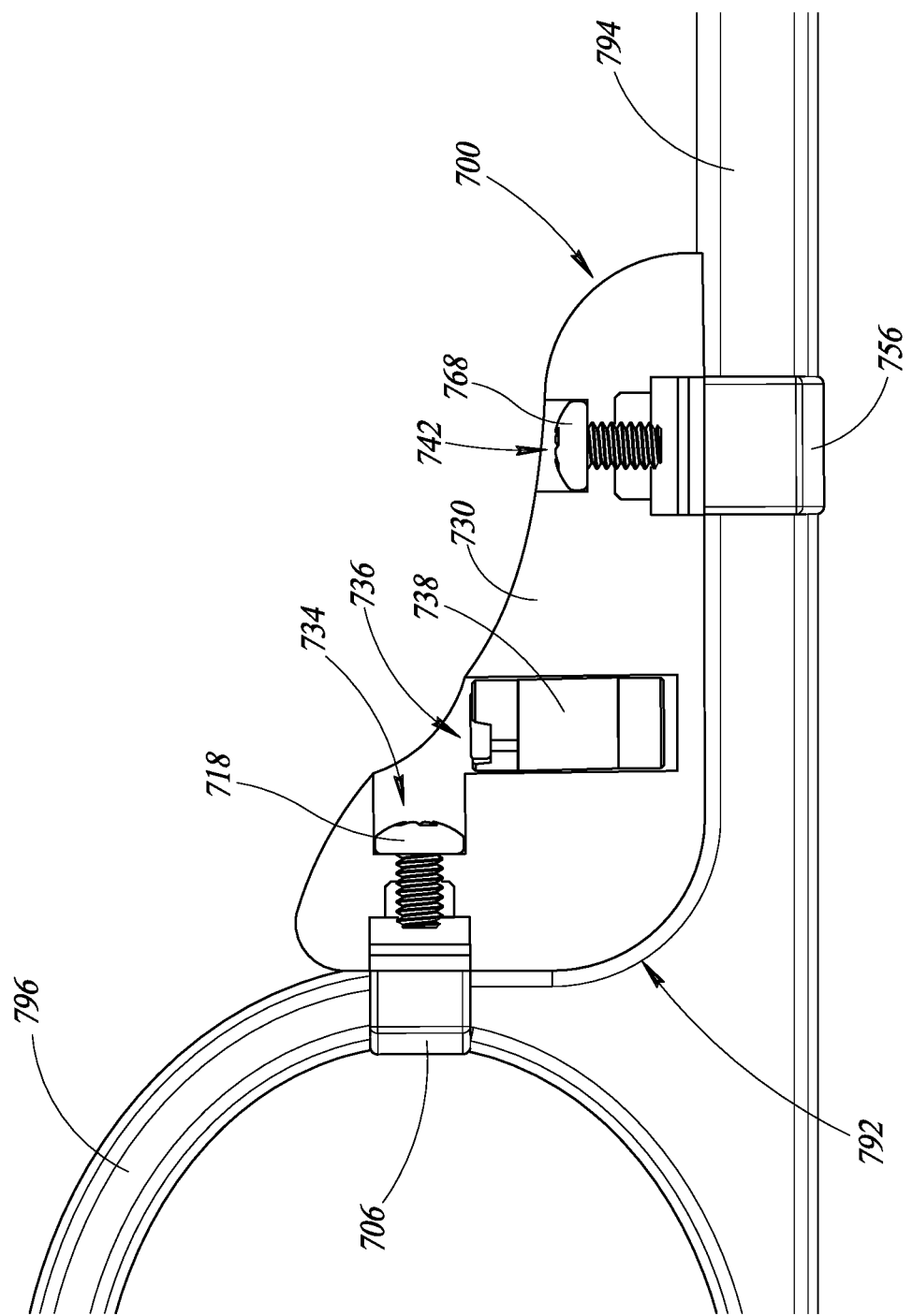
FIG. 17 is a cross-sectional diagram of the apparatus of FIG. 16 physically coupled to a surgical object, according to at least one illustrated embodiment.

FIGS. 16 and 17 show an apparatus 700 that physically couples at least one transponder 738 to a surgical object 790. In particular, FIG. 16 is a side elevational view of the apparatus 700 physically coupled to the surgical object 790. FIG. 17 is a cross-sectional diagram of the apparatus 700 physically coupled to the surgical object 790. The apparatus 700 of FIGS. 16 and 17 is similar in many respects to the apparatus 100 of FIGS. 2-4, and similar or even identical structures may be identified using analogous reference numbers in the figures. As such, certain commonly shared details regarding the materials and/or structure of apparatuses 100 and 700 are not repeated here in detail to avoid unnecessarily obscuring description of the apparatus 700.

The apparatus includes a first channel member 706, a second channel member 756, and a housing 730. The first channel member 706 and the second channel member 756 are respectively physically secured with respect to the housing 732 securingly clamp respective portions of the surgical object 790 in a first channel and a second channel respectively defined thereby. The housing 730 receives at least one transponder.

In particular, FIG. 16 illustrates various spatial features of the apparatus 700. For example, as shown in FIG. 16, the housing 730 sits substantially flush with the surgical object 790. Such may advantageously prevent objects, fluids, contaminants, or other items from reaching or otherwise becoming lodged between the apparatus 700 and the surgical object 790.

An exterior profile of the housing 730 includes a first exterior surface 732 and a second exterior surface 734. The first exterior surface 732 extends parallel to an elongated member 794 of the surgical object 790 and includes an arcuate portion that substantially matches an arcuate surface 792 of the surgical object 790. The arcuate surface 792 is a transition between a finger loop 796 and the elongated member 794. The second exterior surface 734 includes a first convex portion that extends away from the elongated member 794, a second convex portion that extends away from the finger loop 796, and a first concave portion that transitions between the first and the second convex portions.

As best shown in FIG. 17, the housing includes a first passageway 734, a second passageway 736, and a third passageway 742. The first passageway 734 receives a first fastener 718. The first fastener 718 securingly and adjustably engages with the first channel member 706 to clamp a portion of the finger loop 796 in a first channel defined by the first channel member 706. The second passageway receives at least one transponder 738. The third passageway 742 receives a second fastener 768. The second fastener 768 securingly and adjustably engages with the second channel member 756 to clamp a portion of the elongated member 794 and a second channel defined by the second channel member 756.

An encapsulant (not shown) fills the portions of each of passageways 734, 736, and 742 that are respectively unoccupied by the first fastener 718, the transponder 738, and the second fastener 768. The encapsulant may be shaped to substantially match an exterior surface of the housing 730 and thereby contribute to a substantially continuous second exterior surface 734 of the apparatus 700. The encapsulant may ensure that the first fastener 718, the transponder 738, and the second fastener 768 are physically secured in their respective positions and/or prevent contaminants from entering the passageways 734, 736, and 742.

The particular configuration and internal structure of the apparatus 700 illustrated in FIG. 17 is provided as one example configuration only. Other configurations may be used. As an example, in some implementations, one or both of the first channel member 706 and the second channel member 756 are replaced with one or more clips, bands, loops, or other fasteners. For example, the clips may be plastic hooks that are integral to the housing 730.

As another example, in some implementations, the apparatus 700 does not include the first fastener 718 and/or the second fastener 768. For example, the first channel member 706 and/or the second channel member 756 may be physically secured relative to the housing 730 using coupling structures such as those illustrated by FIGS. 11 and 12 and/or FIGS. 13 and 14.

Figure 18:
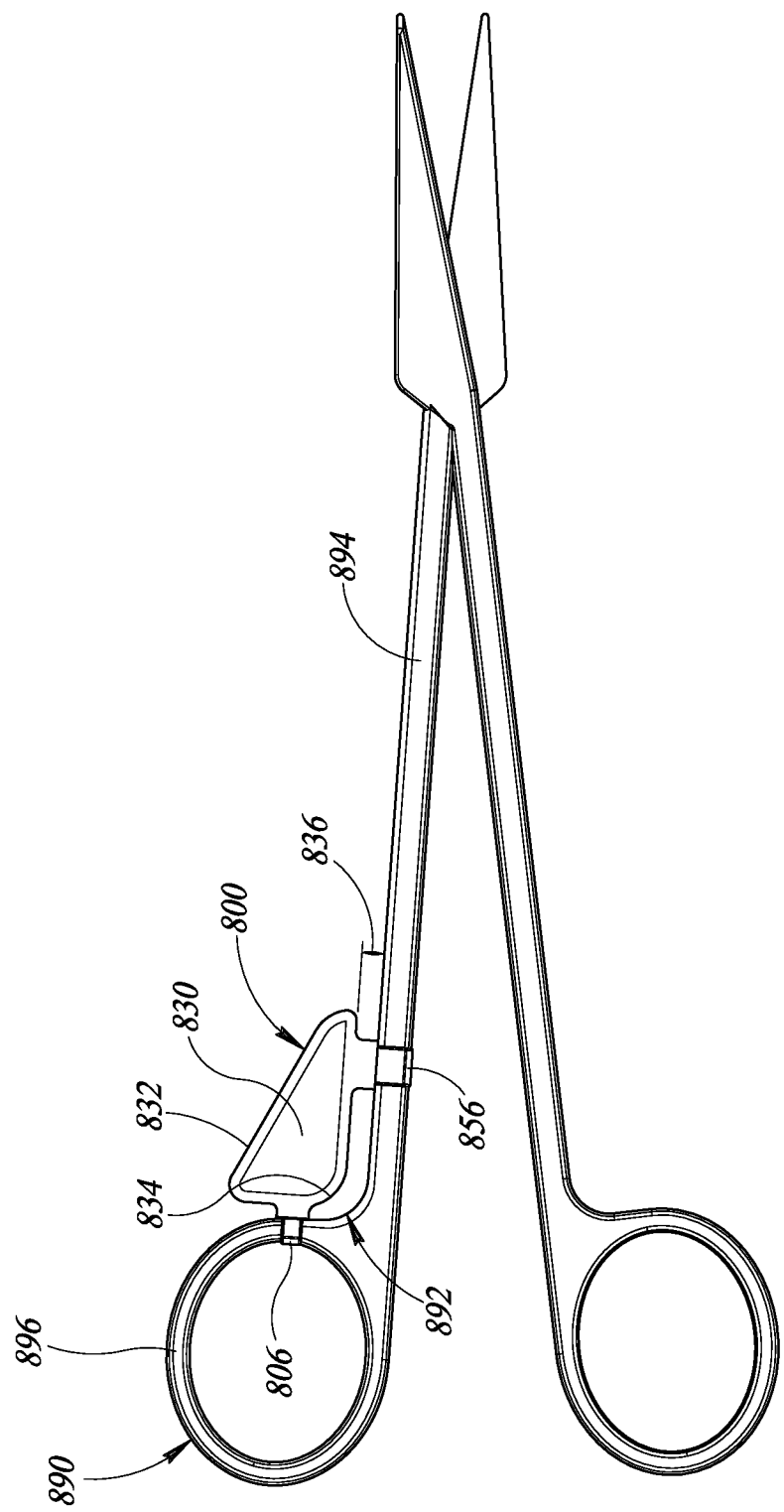
FIG. 18 is a side elevational view of an apparatus physically coupled to a surgical object, according to at least one illustrated embodiment.
Figure 19:
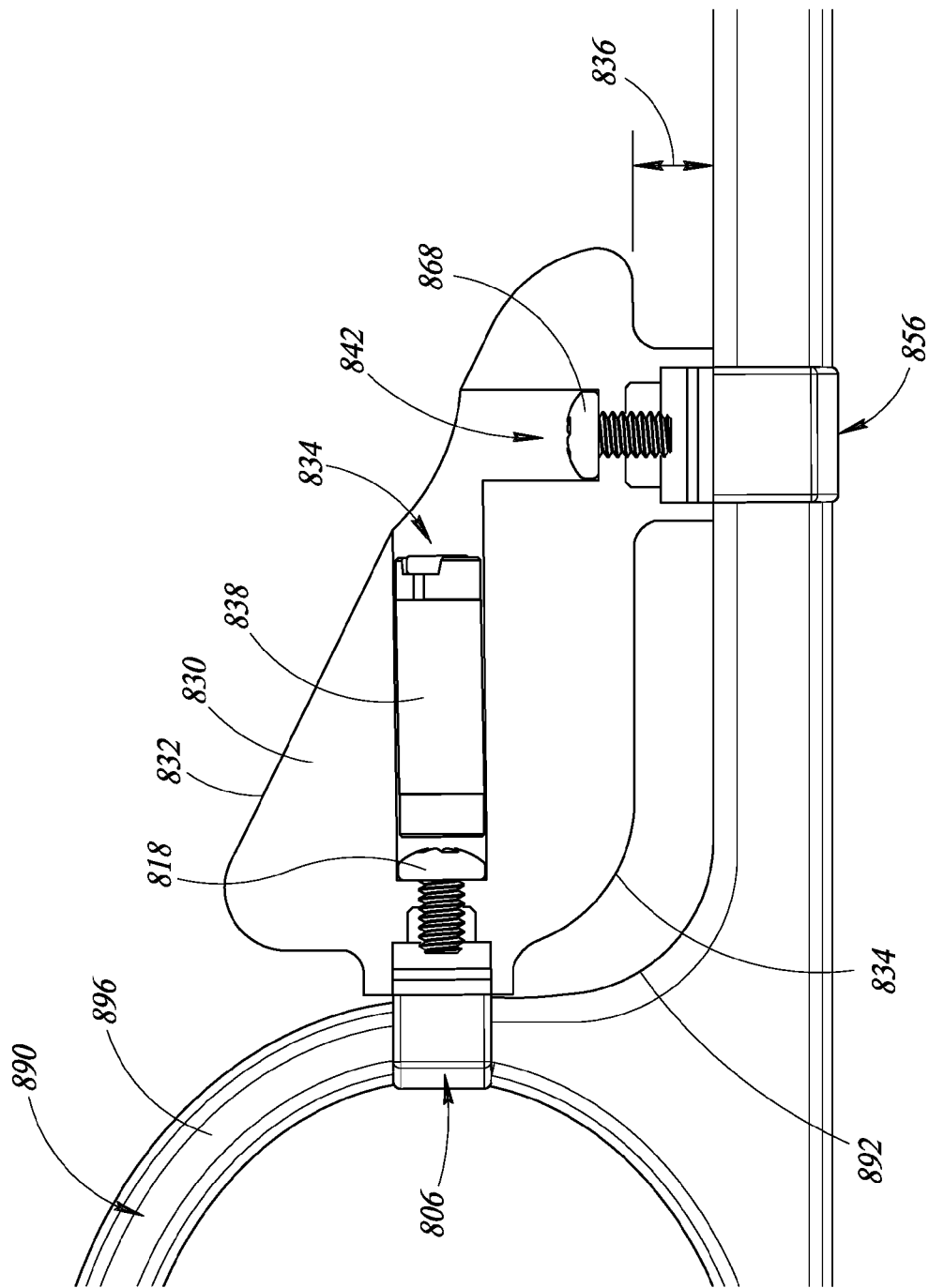
FIG. 19 is a cross-sectional diagram of the apparatus of FIG. 18 physically coupled to a surgical object, according to at least one illustrated embodiment.

FIGS. 18 and 19 show an apparatus 800 that physically couples at least one transponder 838 to a surgical object 890. In particular, FIG. 18 is a side elevational view of the apparatus 800 physically coupled to the surgical object 890. FIG. 19 is a cross-sectional diagram of the apparatus 800 physically coupled to the surgical object 890. The apparatus 800 of FIGS. 18 and 19 is similar in many respects to the apparatus 100 of FIGS. 2-4, and similar or even identical structures may be identified using analogous reference numbers in the figures. As such, certain commonly shared details regarding the materials and/or structure of apparatuses 100 and 800 are not repeated here in detail to avoid unnecessarily obscuring description of the apparatus 800. The apparatus includes a first channel member 806, a second channel member 856, and a housing 830. The first channel member 806 and the second channel member 856 are respectively physically secured with respect to the housing 832 securingly clamp respective portions of the surgical object 890 in a first channel and a second channel respectively defined thereby. The housing 830 receives at least one transponder.

In particular, FIG. 15 illustrates various spatial features of the apparatus 800. For example, as shown in FIG. 15, the housing 830 is substantially spaced a distance 836 from the surgical object 890. Such spacing distance 836 may advantageously help to prevent signal loss due to any metallic portions of the surgical object 890 acting as a Faraday shield or otherwise interfering with wireless communications of the transponder.

An exterior profile of the housing 830 includes a first exterior surface 832 and a second exterior surface 834. The first exterior surface 832 extends curvedly away from an elongated member 894 of the surgical object 890 and then extends towards a finger loop 896 of the surgical object 890. The second exterior surface 834 extends from the first exterior surface 832 towards the elongated member 894 and includes an arcuate portion that substantially matches an arcuate surface 892 of the surgical object 890. The arcuate surface 892 is a transition between the finger loop 896 and the elongated member 894.

As best shown in FIG. 19, the housing includes a first passageway 834 and a second passageway 842. The first passageway 834 receives a first fastener 818. The first fastener 818 securingly and adjustably engages with the first channel member 806 to clamp a portion of the finger loop 896 in a first channel defined by the first channel member 806. The first passageway further receives at least one transponder 838. The second passageway 842 receives a second fastener 868. The second fastener 868 securingly and adjustably engages with the second channel member 856 to clamp a portion of the elongated member 894 and a second channel defined by the second channel member 856.

An encapsulant (not shown) fills the portions of each of passageways 834 and 842 that are respectively unoccupied by the first fastener 818 and the transponder 838 and the second fastener 868. The encapsulant may be shaped to substantially match the exterior surface of the housing 830 and thereby contribute to a substantially continuous first exterior surface 832 of the apparatus 800. The encapsulant may ensure that the first fastener 818, the transponder 838, and the second fastener 868 are physically secured in their respective positions and/or prevent contaminants from entering the passageways 834 and 842.

The particular configuration and internal structure of the apparatus 800 illustrated in FIG. 19 is provided as one example configuration only. Other configurations may be used. As an example, in some implementations, one or both of the first channel member 806 and the second channel member 856 are replaced with one or more clips, bands, loops, or other fasteners. For example, the clips may be plastic hooks that are integral to the housing 830.

As another example, in some implementations, the apparatus 800 does not include the first fastener 818 and/or the second fastener 868. For example, the first channel member 806 and/or the second channel member 856 may be physically secured relative to the housing 830 using coupling structures such as those illustrated by FIGS. 11 and 12 and/or FIGS. 13 and 14.

Figure 20:
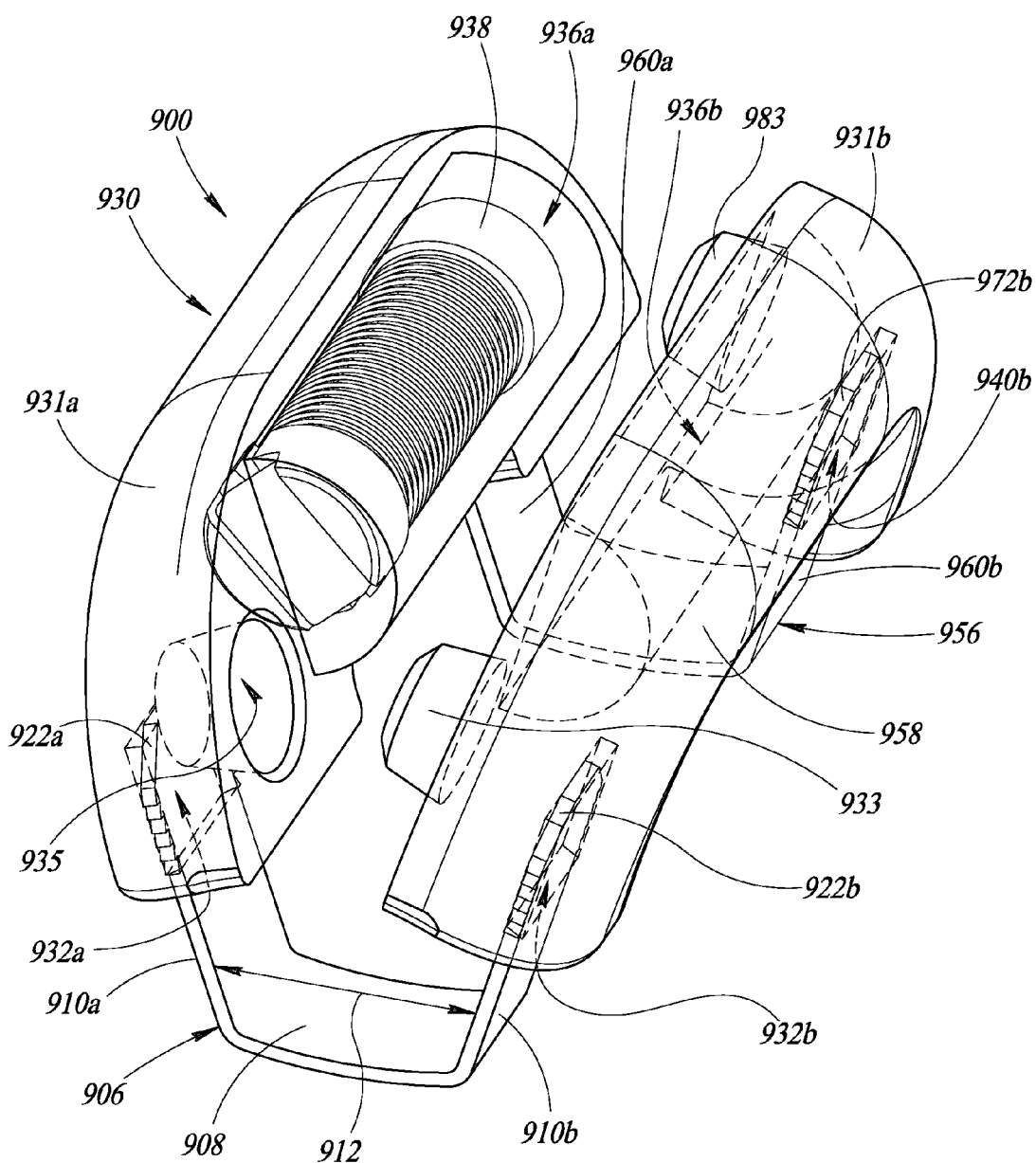
FIG. 20 is an isometric view of an apparatus to physically couple one or more transponders to a surgical object, according to at least one illustrated embodiment.
Figure 21:
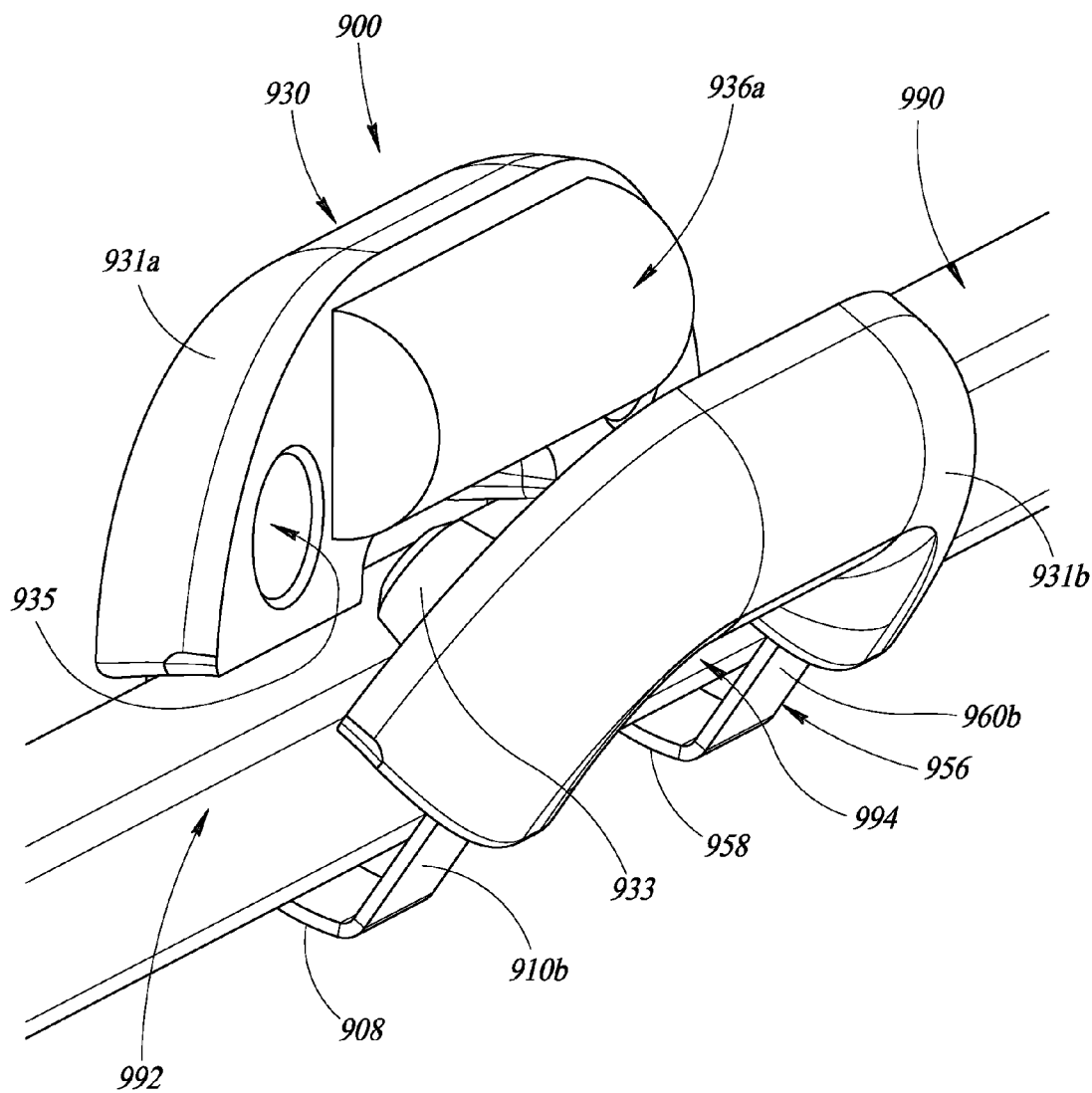
FIG. 21 is an isometric view of the apparatus of FIG. 20 physically coupled to a surgical object, according to at least one illustrated embodiment.
Figure 22:
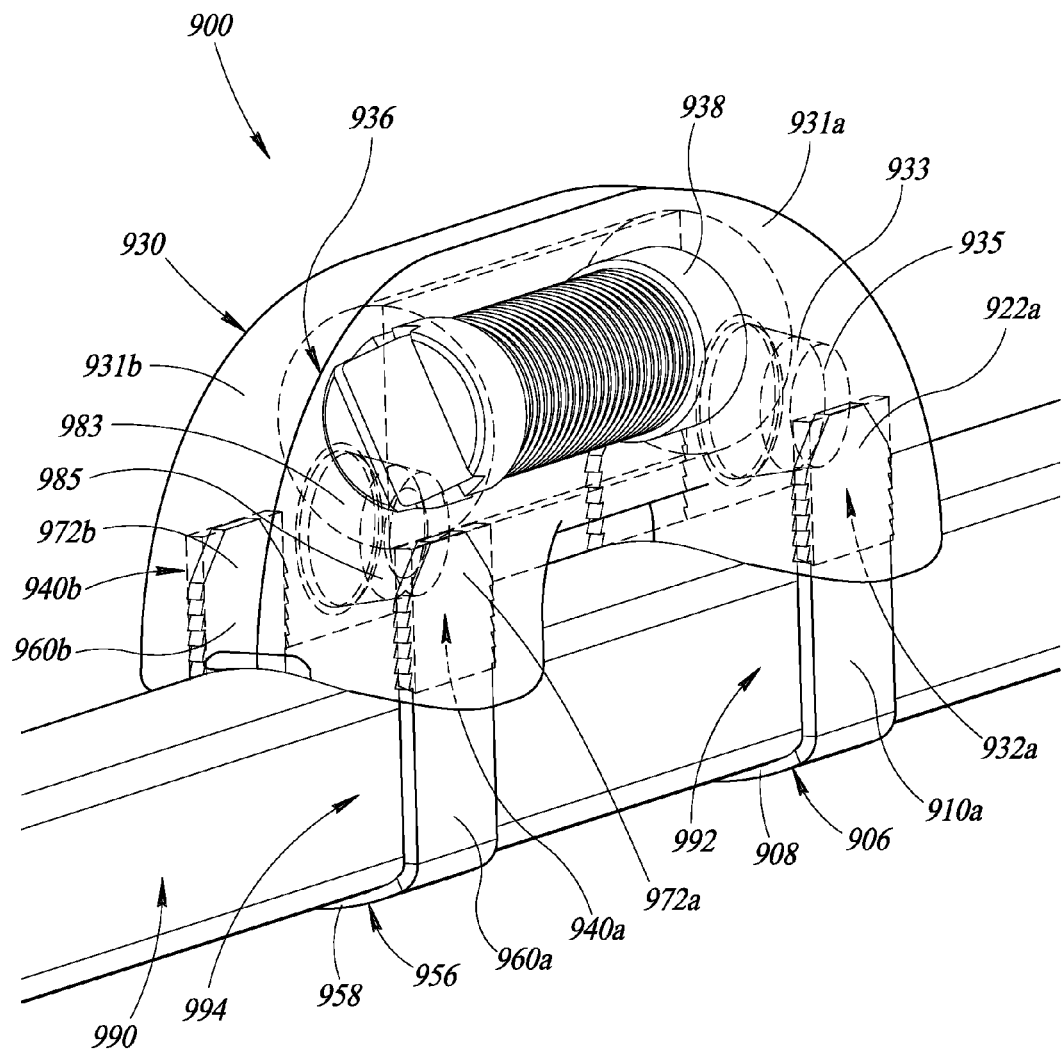
FIG. 22 is an isometric view of the apparatus of FIG. 20 physically coupled to a surgical object, according to at least one illustrated embodiment.
Figure 23:
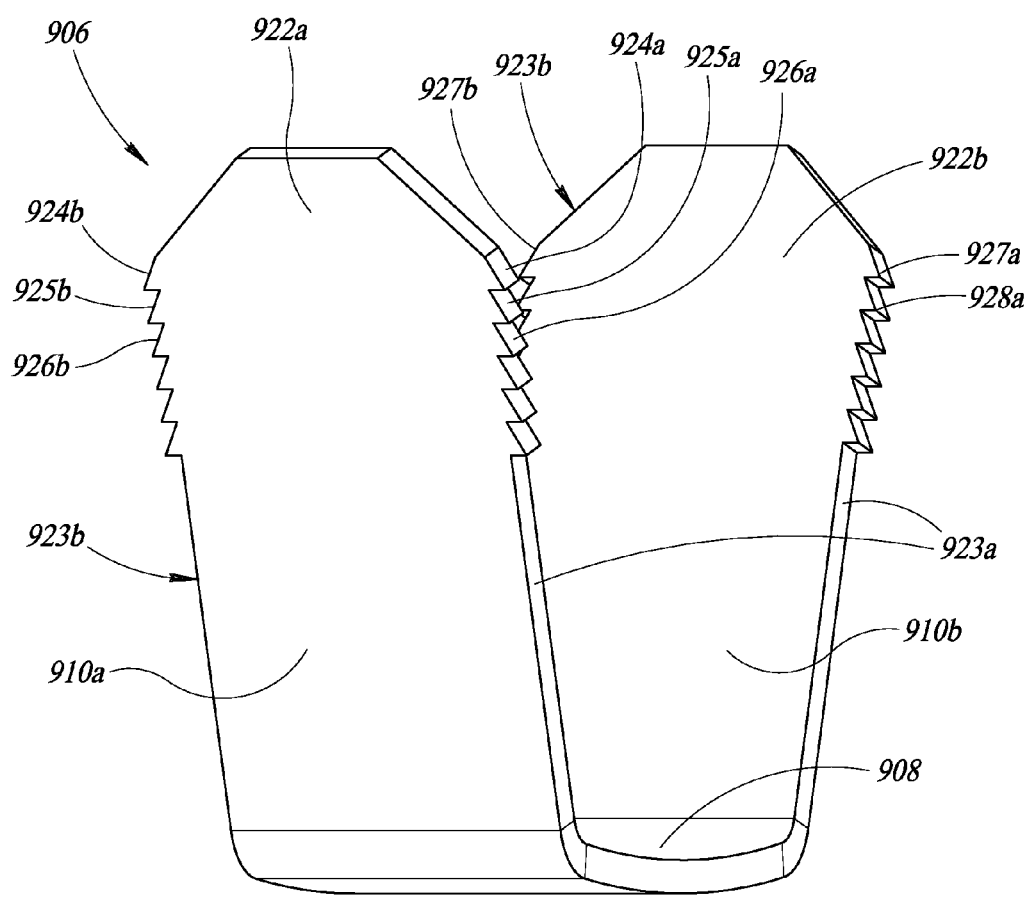
FIG. 23 is an isometric view of a channel member of the apparatus of FIG. 20, according to at least one illustrated embodiment.

FIGS. 20-22 show an apparatus 900 to physically couple at least one transponder 938 to a surgical object 990. In particular, FIG. 20 shows the apparatus 900 not physically coupled to the surgical object 990 while FIGS. 21-22 show the apparatus 900 physically coupled to the surgical object 990. FIG. 23 is an isometric view of a first channel member 906 of the apparatus 900, according to at least one illustrated embodiment.

The apparatus 900 is similar in many respects to the apparatus 100 of FIGS. 2-4, and similar or even identical structures may be identified using analogous reference numbers in the figures. As such, certain commonly shared details regarding the materials and/or structure of apparatuses 100 and 900 are not repeated here in detail to avoid unnecessarily obscuring description of the apparatus 900.

The apparatus 900 includes a first channel member 906, a second channel member 956, and a housing 930. In each of FIGS. 20 and 22 the housing 930 is transparently depicted for the purposes of illustrating certain features of the apparatus 900 internal to the housing 930. However, the housing 930 is typically not transparent. For example, the housing 930 is not transparently depicted in FIG. 21.

The housing 930 includes a female body portion 931a and a male body portion 931b. The male body portion 931b has a first member 933 and a second member 983 that respectively extend from the male body portion 931b towards the female body portion 931a. For example, the first member 933 and the second member 983 may be conical frustums. However, the first member 933 and the second member 983 may have other shapes, including, as example, rivets, snaps, hooks, male buckle portions, clasps, or other fasteners. In addition, although two members 933 and 983 are shown, the male body portion 931b may have any number of members.

The female body portion 931a includes a first slot 935 that is sized and shaped to fittingly receive the first member 933 and includes a second slot 985 that is sized and shaped to fittingly receive the second member 983. For example, the first and the second slots 935 and 985 may respectively physically engage the first and the second members 933 and 983 using an interference fit or by one or more detent mechanisms (e.g., teeth or female buckle portions).

The housing 930 is adjustable between a closed configuration and an open configuration. When the housing 930 is in the closed configuration, as shown in FIG. 22, the first and the second members 933 and 983 are respectively received by and physically engaged with the first and the second slots 935 and 985. When the housing 930 is in the open configuration, as shown in FIGS. 20 and 22, the first and the second members 933 and 983 are respectively not received by or physically engaged with the first and the second slots 935 and 985.

The housing 930 further includes a transponder receiving cavity 936. In particular, the female body portion 931a includes a first transponder receiving cavity portion 936a that receives at least one transponder 938. For example, the first transponder receiving cavity portion 936a may be a cylindrical cavity defined at least in part by a convex semi-cylindrical surface that extends from the female body portion 931a towards the male body portion 931b. Further, the male body portion 931b includes a second transponder receiving cavity portion 936b that is shaped and sized to receive the first transponder receiving cavity portion 936a when the housing 930 is in the closed configuration. For example, the second transponder receiving cavity portion 936b may be formed by a concave semi-cylindrical surface that extends into the male body portion 931b. However, in some implementations, the male body portion 931b includes the first transponder receiving cavity portion 936a and the female body portion 931a includes the second transponder receiving cavity portion 936b.

In some implementations, the first transponder receiving cavity portion 936a is accessible (e.g., openable and closeable) by a user to insert or remove the transponder 938 from the first transponder receiving cavity portion 936a. For example, the convex semi-cylindrical surface may be physically coupled to the female body portion 931a using a hinge structure and a clasp or may otherwise be separable from the female body portion 931a via other mechanisms to permit access to the first transponder receiving cavity portion 936a. In such implementations, the transponder 938 may or may not be potted into the first transponder receiving cavity portion 936a using an encapsulant. In other implementations, the female body portion 931a is a single integral and molded structure and the transponder 938 is molded into the first transponder receiving cavity portion 936a.

The first channel member 906 has a first base 908 and a first pair of side portions 910a and 910b that extend from the first base 908. The first pair of side portions 910a and 910b are opposed to one another across a width 912 of the first channel member 906 to form a first channel therebetween. The width 912 of the first channel is sized to receive at least a first portion 992 of the surgical object 990 therein.

The first channel member 906 is respectively physically coupled to the female body portion 931a and the male body portion 931b at a first pair of ends 922a and 922b of the first pair of side portions 910a and 910b. The first pair of ends 922a and 922b of the first pair of side portions 910a and 910b are opposite the first base 908.

More particularly, the female body portion 931a and the male body portion 931b respectively have a first pair of cavities 932a and 932b to respectively receive at least the first pair of ends 922a and 922b of the first pair of side portions 910a and 910b.

As best shown in FIG. 23, the first channel member 906 has a first edge 923a and a second edge 923b that is opposite the first edge 923a. Each of the first pair of ends 922a and 922b has a plurality of teeth along both the first and the second edges 923a and 923b (only certain teeth numerically called out to avoid obscuring the illustration). The teeth are angled towards the first base 908.

As one example, the end 922a of side portion 910a includes six pairs of teeth respectively along the first and the second edges 923a and 923b (only three pairs called out as 924a and 924b, 925a and 925b, and 926a and 926b). Likewise, the end 922b of the side portion 910b includes six pairs of teeth respectively along the first and the second edges 923a and 923b (only one tooth 927b fully visible on edge 923b; only two teeth 927a and 927b called out on edge 923a). Although each end 922a and 922b includes six pairs of teeth, any number of teeth can be included.

As best shown in FIG. 20, the first pair of cavities 932a and 932b respectively define a first pair of interior surfaces within the female body portion 931a and the male body portion 931b, respectively. When the first pair of ends 922a and 922b are respectively received in the first pair of cavities 932a and 932b, at least the respective pluralities of teeth of the first pair of ends 922a and 922b respectively physically engage with the first pair of interior surfaces of the female body portion 931a and the male body portion 931b.

Similar to first channel member 906 and as best shown in FIG. 22, the second channel member 956 has a second base 958 and a second pair of side portions 960a and 960b that extend from the second base 958. The second pair of side portions 960a and 960b are opposed to one another across a width of the second channel member 956 to form a second channel therebetween. The width of the second channel is sized to receive at least a second portion 994 of the surgical object 990 therein.

The second channel member 956 is respectively physically coupled to the female body portion 931a and the male body portion 931b at a second pair of ends 972a and 927b of the second pair of side portions 960a and 960b. The second pair of ends 972a and 972b of the second pair of side portions 960a and 960b are opposite the second base 958. More particularly, the female body portion 931a and the male body portion 931b respectively have a second pair of cavities 940a and 940b to respectively receive at least the second pair of ends 972a and 927b of the second pair of side portions 960a and 960b.

As best shown in FIG. 22, the second pair of cavities 940a and 940b respectively define a second pair of interior surfaces within the female body portion 931a and the male body portion 931b, respectively. When the second pair of ends 972a and 972b are respectively received in the second pair of cavities 940a and 940b, at least the respective pluralities of teeth of the second pair of ends 972a and 972b respectively physically engage with the second pair of interior surfaces of the female body portion 931a and the male body portion 931b.

The first channel member 906 and the second channel member 956 are resilient to permit repeated adjustment of the housing 930 between the closed configuration and the open configuration. For example, the first channel member 906 and the second channel member 956 may be rigid but resilient metal bands.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other metallic implements, other types of transponders, and other interrogation and detection systems. For instance, the apparatuses of the present disclosure may be used to mark implements anytime identification and/or detection of the presence of marked objects is desirable in a confined area, not just during surgery. For example, it may be used to make sure marked tools are not left inside a machine (e.g., vehicle, copy machine, etc.) after maintenance is performed. In at least some embodiments, the apparatuses of the present disclosure may be utilized to mark objects to determine the removal of a marked implement from a confined area, such as a chef knife from a kitchen of an airport restaurant or computers from a server room. In such an embodiment, an interrogation device, for example, may be placed proximate to a door of the confined area.

In addition, an apparatus may be manufactured and distributed for tagging objects without a transponder currently attached. Advantageously, a transponder compatible with a particular detection and interrogation system may then be introduced or inserted into the apparatus at a subsequent time, including by the end-user.

Those of skill in the art will recognize that many of the methods or algorithms set out herein may employ additional acts, may omit some acts, and/or may execute acts in a different order than specified.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, if any, including but not limited to U.S. Pat. No. 6,026,818, issued Feb. 22, 2000; U.S. Patent Publication No. US 2004/0250819, published Dec. 16, 2004; U.S. Provisional Patent Application Ser. No. 60/811,376, filed Jun. 6, 2006; U.S. Provisional Patent Application Ser. No. 60/892,208, filed Feb. 28, 2007; and U.S. Provisional Patent Application Ser. No. 62/121,358, filed Feb. 26, 2015 are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An apparatus to physically couple one or more transponders to a surgical object used in a surgical environment, the apparatus comprising:
   at least one transponder that wirelessly receives and returns signals;
   at least a first clamp comprising a first fastener and a first channel member, the first channel member having a first base and a first pair of side portions that extend from the first base and which are opposed to one another across a width of the first channel member to form a first channel therebetween, the width of the first channel sized to receive at least a first portion of a surgical object therein, wherein the first fastener adjustably engages with the first channel member to securingly clamp the first portion of the surgical object in the first channel of the first channel member;
   a housing that has at least a first cavity that receives at least a portion of the first pair of side portions of the first channel member, a first passageway that receives the first fastener and opens at least in part into the first cavity to permit the first fastener to extend at least in part into the first cavity and adjustably engage with the first channel member, and a second passageway that receives the at least one transponder; and
   a second clamp comprising a second fastener and a second channel member, the second channel member having a second base and a second pair of side portions that extend from the second base and which are opposed to one another across a width of the second channel member to form a second channel therebetween, the width of the second channel sized to receive at least a second portion of the surgical object therein, wherein the second fastener adjustably engages with the second channel member to securingly clamp the second portion of the surgical object in the second channel of the second channel member,
   wherein the housing has a second cavity that receives at least a portion of the second pair of side portions of the second channel member and a third passageway that receives the second fastener and opens at least in part into the second cavity to permit the second fastener to extend at least in part into the second cavity and adjustably engage with the second channel member.

2. The apparatus of claim 1 wherein the first passageway extends in a first direction, the second passageway extends in a second direction, and the third passageway extends in a third direction, the third direction parallel to the first direction, the second direction non-parallel with respect to the first and the third directions.

3. The apparatus of claim 1 wherein the first fastener and the second fastener respectively have an elongated shaft that has a first diameter and a head that has a second diameter that is greater than the first diameter, and the first passageway and the third passageway respectively have an outer portion that has a third diameter that is greater than the second diameter and an inner portion that has a fourth diameter that is greater than the first diameter and less than the second diameter.

4. The apparatus of claim 3 wherein the second passageway intersects the top portion of the first passageway, the second passageway having a fifth diameter at least greater than the second diameter.

5. The apparatus of claim 3 wherein the second passageway intersects the inner portion of the first passageway, the second passageway having a fifth diameter at least greater than the first diameter.

6. The apparatus of claim 3 wherein the housing forms a first shelf at a first transition between the outer portion and the inner portion of the first passageway, the first shelf physically engages the head of the first fastener, the housing forms a second shelf at a second transition between the outer portion and the inner portion of the third passageway, and the second shelf physically engages the head of the second fastener.

7. The apparatus of claim 1 wherein a length of each of the first pair of side portions taperedly increases as the respective side portion extends away from the first base.

8. The apparatus of claim 1, further comprising:
   an encapsulant that fills at least one of the first passageway or the second passageway.

9. The apparatus of claim 8 wherein the encapsulant is capable of withstanding sterilization of the apparatus by one or more of autoclaving, electron beam or isotope radiation, ethylene oxide, plasma or corona discharge, and liquid sterilants.

10. The apparatus of claim 8 wherein the encapsulant comprises a biocompatible epoxy.

11. An apparatus to physically couple one or more transponders to a surgical object used in a surgical environment, the apparatus comprising:
   at least a first clamp comprising a first fastener and a first channel member, the first channel member having a first base and a first pair of side portions that extend from the first base and which are opposed to one another across a width of the first channel member to form a first channel therebetween, the width of the first channel sized to receive at least a first portion of a surgical object therein, wherein the first fastener adjustably engages with the first channel member to securingly clamp the first portion of the surgical object in the first channel of the first channel member; and a housing that has at least a first cavity that receives at least a portion of the first pair of side portions of the first channel member, a first passageway that receives the first fastener and opens at least in part into the first cavity to permit the first fastener to extend at least in part into the first cavity and adjustably engage with the first channel member, and a second passageway to receive at least one transponder that wirelessly receives and returns signals, wherein the first fastener comprises a first externally threaded screw and a first internally threaded nut that securingly receives the first externally threaded screw, the first channel member further comprises a first pair of flanges that respectively extend from the first pair of side portions into the first channel, and the first internally threaded nut is positioned one of i) between the first pair of flanges and the first base, wherein the first internally threaded nut physically engages the first pair of flanges or ii) opposite the first pair of flanges from the first base.

12. An apparatus to physically couple one or more transponders to a surgical object used in a surgical environment, the apparatus comprising:

at least a first clamp comprising a first fastener and a first channel member, the first channel member having a first base and a first pair of side portions that extend from the first base and which are opposed to one another across a width of the first channel member to form a first channel therebetween, the width of the first channel sized to receive at least a first portion of a surgical object therein, wherein the first fastener adjustably engages with the first channel member to securingly clamp the first portion of the surgical object in the first channel of the first channel member; and a housing that has at least a first cavity that receives at least a portion of the first pair of side portions of the first channel member, a first passageway that receives the first fastener and opens at least in part into the first cavity to permit the first fastener to extend at least in part into the first cavity and adjustably engage with the first channel member, and a second passageway to receive at least one transponder that wirelessly receives and returns signals, wherein the first fastener comprises a first screw that has first external threading, and the first channel member further comprises a first pair of flanges that respectively extend from the first pair of side portions into the first channel and engage the first external threading of the first screw.

13. The apparatus of claim 12 wherein the first pair of flanges respectively have respective end portions that are respectively angled towards the first base of the first channel member and engage the first external threading of the first screw.

14. An apparatus to physically couple one or more transponders to a surgical object used in a surgical environment, the apparatus comprising:

at least a first clamp comprising a first fastener and a first channel member, the first channel member having a first base and a first pair of side portions that extend from the first base and which are opposed to one another across a width of the first channel member to form a first channel therebetween, the width of the first channel sized to receive at least a first portion of a surgical object therein, wherein the first fastener adjustably engages with the first channel member to securingly clamp the first portion of the surgical object in the first channel of the first channel member; and a housing that has at least a first cavity that receives at least a portion of the first pair of side portions of the first channel member, a first passageway that receives the first fastener and opens at least in part into the first cavity to permit the first fastener to extend at least in part into the first cavity and adjustably engage with the first channel member, and a second passageway to receive at least one transponder that wirelessly receives and returns signals, wherein the first channel member further comprises a first pair of flanges that respectively extend from the first pair of side portions into the first channel and respectively have a through-hole extending therethrough, the respective through-holes of the first pair of flanges are aligned, and the first fastener extends through the through-holes of the first pair of flanges.

15. A method to physically couple one or more transponders to a surgical object usable in a surgical environment, the method comprising:

positioning a first portion of a surgical object into a first channel formed by a first channel member, the first channel member having a first base and a first pair of side portions that extend from the first base and which are opposed to one another across a width of the first channel member to form the first channel therebetween;

positioning a housing that has a first cavity, a first passageway that opens at least in part into the first cavity, and a second passageway therein to receive at least a portion of the first pair of side portions in the first cavity, the second passageway sized to receive at least one transponder;

inserting a first fastener into the first passageway to engage the first channel member, wherein inserting a first fastener comprises inserting a first screw that has first external threading into the first passageway; and adjusting a first engagement between the first fastener and the first channel member to securingly clamp the first portion of the surgical object in the first channel of the first channel member, wherein adjusting a first engagement comprises rotating the first screw to engage the first external threading of the first screw with one or more of i) a first and a second lip of the first channel member that respectively extend from the first pair of side portions into the first channel and ii) a first nut located above or below the first and the second lip and engaged therewith.

16. The method of claim 15, further comprising:

adjusting the first engagement to release the first portion of the surgical object from the first channel of the first channel member; and removing the housing from the surgical object.

17. The method of claim 15, further comprising:

positioning a second portion of the surgical object into a second channel formed by a second first channel member, the second channel member having a second base and a second pair of side portions that extend from the second base and which are opposed to one another across a width of the second channel member to form the second channel therebetween;

positioning the housing to receive at least a portion of the second pair of side portions in a second cavity of the housing;

inserting a second fastener into a third passageway of the housing to engage the second channel member; and adjusting a second engagement between the second fastener and the second channel member to securingly clamp the second portion of the surgical object in the second channel of the second channel member.

18. The method of claim 15, further comprising:

inserting the at least one transponder into the second passageway.

19. The method of claim 18 wherein inserting the at least one transponder into the second passageway comprises inserting the at least one transponder into the second passageway that intersects with the first passageway to move the at least one transponder past the first passageway.

20. The method of claim 15, further comprising:

filling each of the first and the second passageways with an encapsulant.

* * * * *